(12) United States Patent
Colby et al.

(10) Patent No.: US 9,359,277 B2
(45) Date of Patent: Jun. 7, 2016

(54) COMPOSITIONS AND PROCESSES OF PREPARING AND USING THE SAME

(75) Inventors: David A. Colby, West Lafayette, IN (US); Mark V. Riofski, Evanston, IL (US); Changho Han, Nashville, TN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 14/006,386

(22) PCT Filed: Mar. 22, 2012

(86) PCT No.: PCT/US2012/030089
§ 371 (c)(1),
(2), (4) Date: Oct. 16, 2013

(87) PCT Pub. No.: WO2012/129384
PCT Pub. Date: Sep. 27, 2012

(65) Prior Publication Data
US 2014/0039182 A1  Feb. 6, 2014

Related U.S. Application Data

(60) Provisional application No. 61/467,778, filed on Mar. 25, 2011, provisional application No. 61/466,147, filed on Mar. 22, 2011.

(51) Int. Cl.
| | | |
|---|---|---|
| C07C 45/00 | (2006.01) | |
| C07C 49/83 | (2006.01) | |
| C07C 49/173 | (2006.01) | |
| C07C 29/38 | (2006.01) | |
| C07D 317/54 | (2006.01) | |
| C07C 41/30 | (2006.01) | |
| C07C 303/40 | (2006.01) | |
| C07C 201/12 | (2006.01) | |
| C07B 37/04 | (2006.01) | |
| C07C 45/45 | (2006.01) | |
| C07C 45/67 | (2006.01) | |
| C07C 45/72 | (2006.01) | |
| C07C 49/24 | (2006.01) | |
| C07C 49/82 | (2006.01) | |
| C07D 317/46 | (2006.01) | |
| C07D 487/04 | (2006.01) | |

(52) U.S. Cl.
CPC .............. *C07C 45/008* (2013.01); *C07B 37/04* (2013.01); *C07C 29/38* (2013.01); *C07C 41/30* (2013.01); *C07C 45/455* (2013.01); *C07C 45/673* (2013.01); *C07C 45/72* (2013.01); *C07C 49/173* (2013.01); *C07C 49/24* (2013.01); *C07C 49/82* (2013.01); *C07C 49/83* (2013.01); *C07C 201/12* (2013.01); *C07C 303/40* (2013.01); *C07D 317/46* (2013.01); *C07D 317/54* (2013.01); *C07D 487/04* (2013.01); *C07C 2101/14* (2013.01); *C07C 2102/18* (2013.01); *C07C 2102/42* (2013.01); *C07C 2103/18* (2013.01); *C07C 2103/74* (2013.01)

(58) Field of Classification Search
None
See application file for complete search history.

(56) References Cited

U.S. PATENT DOCUMENTS

| | | | |
|---|---|---|---|
| 4,544,772 A | 10/1985 | Sawai et al. | |
| 4,564,716 A | 1/1986 | Katsuhara et al. | |
| 4,734,169 A | 3/1988 | Yokoi et al. | |
| 5,210,248 A | 5/1993 | Babirad et al. | |
| 5,750,517 A * | 5/1998 | Baggiolini et al. | ........... 514/167 |
| 6,114,487 A | 9/2000 | Kobayashi et al. | |
| 2004/0087627 A1 | 5/2004 | Arrhenius et al. | |
| 2004/0186322 A1 * | 9/2004 | Ohtsuka et al. | ............... 568/393 |
| 2008/0262273 A1 | 10/2008 | Yamamoto et al. | |

OTHER PUBLICATIONS

Ghosh, DBU (1,8-diazabicyclo[5.4.0]undec-7-ene)—A Nucleophillic Base, Synlett, 2004, 3, pp. 0574-0575.*
Badio et al. "Synthesis and nicotinic activity of epiboxidine: an isoxazole analogue of epibatidine", Eur. J. Pharmacol. 1997, 321, 189-194.
Guan et al. "Highly Selective Aerobic Oxidation of Alcohol Catalyzed by a Gold(I) Complex with an Anionic Ligand", J. Am. Chem. Soc. 2005, 127, 18004-18005.
Baumann et al. "Development of fluorination methods using continuous-flow microreactors", Tetrahedron 2009, 65, 6611.
Crich et al. "Photoinduced Free Radical Chemistry of the Acyl Tellurides: Generation, Inter- and Intramolecular Trapping, and ESR Spectroscopic Identification of Acyl Radicals", J. Am. Chem. Soc. 1994, 116, 8937-8951.
Danheiser et al. "An improves method for the synthesis of .alpha.-diazo ketones", J. Org. Chem. 1990, 55, 1959-1964.
Drew et al. "Synthesis from pregnenolone of fluorescent cholesterol analog probes with conjugated unsaturation in the side chain", J. Org. Chem. 1987, 52, 4047-4052.
Folleas et al. "Fluoroform: an Efficient Precursor for the Trilluoromethylation of Aldehydes", Tetrahedron, 2000, 56, 275-283.
Fukuda et al. "Synthesis of chiral difluorinated [6]-gingerol", Tetrahedron 1996, 52, 157-164.
Hoye et al. "Long-range shielding effects in the (1)H NMR spectra of Mosher-like ester derivatives", Org. Lett. 2010, 12, 1768-1771.
International Search Report for PCT Application No. PCT/US2012/030089 mailed Oct. 31, 2012.
Izzo et al. "Efficient Stereocontrolled Access to 15- and 16-Hydroxy Steroids", Eur. J. Org. Chem. 1999, 3505-3510.

(Continued)

*Primary Examiner* — San-Ming Hui
*Assistant Examiner* — Andrew Lee
(74) *Attorney, Agent, or Firm* — Mark S. Cohen; Pearl Cohen Zedek Latzer Baratz LLP

(57) ABSTRACT

The present invention relates to compositions, for example, the DBU/Hexafluoroacetone hydrate salt, and processes of preparing and using the same for the modification of chemical compounds via the release of trifluoroacetate. The DBU/Hexafluoroacetone hydrate salt can perform trifluoromethylation reactions on chemical compounds, such as carbonyl group-containing compounds.

20 Claims, No Drawings

(56) References Cited

OTHER PUBLICATIONS

Kang et al. "Palladium-Catalyzed Carbonylative Coupling of Iodonium Salts with Organostannanes under Aqueous Conditions: Synthesis of Unsymmetrical Vinyl and Aromatic Ketones", Synthesis 1998, 823-825.

Prakash et al. "Difluoromethyl Phenyl Sulfone as a Selective Difluoromethylene Dianion Equivalent: One-Pot Stereoselective Synthesis of anti-2,2-Difluoropropane-1,3-diols", Angew. Chem. Int. Ed. 2003, 42, 5216.

Rodrigues et al. "Preparation of α-Methylene Ketones by Direct Methylene Transfer", Synth. Commun. 2003, 33, 331-340.

Sauer et al. "Direct Carbon-Carbon Bond Formation via Reductive Soft Enolization: A Kinetically Controlled syn-Aldol Addition of r-Halo Thioesters and Enolizable Aldehydes", J. Am. Chem. Soc. 2010, 132, 13997-13999.

Seco et al. "The Assignment of Absolute Configuration by NMR", Chem. Rev. 2004, 104, 17-117.

Sloop et al. "Keto-enol and enol-enol tautomerism in trifluoromethyl-β-diketones", J. Fluorine Chem. 2006, 127, pp. 780-786.

Takagi et al. "Determination of the absolute configuration of party fluorinated allytic alcohols: the first synthesis of optically pure 1,2-difluoroallytic alcohols", Tetrahedron Lett. 2000, 41, 7889-7892.

Tonari et al. "Synthesis and Antibacterial Activity of α-Methylenecamphor and Isophorone Derivatives", J. Oleo Sci. 2002, 52, 255-258.

\* cited by examiner

COMPOSITIONS AND PROCESSES OF PREPARING AND USING THE SAME

CROSS-REFERENCE TO RELATED APPLICATIONS

This application is a National Phase Application of PCT International Application No. PCT/US12/30089, filed on Mar. 22, 2012, claiming the benefit of U.S. Provisional Patent Application Ser. No. 61/466,147, filed on Mar. 22, 2011 and U.S. Provisional Patent Application Ser. No. 61/467,778, filed on Mar. 25, 2011, all of which are incorporated herein by reference in their entirety.

TECHNICAL FIELD

The invention relates to compositions and processes of preparing and using the same for the modification of chemical compounds via the release of trifluoroacetate. The compositions of the invention are useful for the preparation of important building blocks in drug development.

BACKGROUND OF THE INVENTION

The incorporation of fluorine into fine chemicals has had a significant impact in the chemical, agrochemical, and pharmaceutical industries. For example, difluoromethyl groups may serve as bioisosteric replacements and surrogates for oxygen in compounds, providing greater stability (Blackburn, et al. *J. Chem. Soc. Chem. Commun.* 1981, 930) and as useful blocking groups (Fukuda, et al. *Tetrahedron* 1996, 52, 157). Drug candidates that contain trifluoromethyl groups, compared to non-fluorinated counterparts, often display better biological activities, including increased lipophilicity, bioavailability, binding affinity, metabolic stability, and membrane permeability (Ojima, et al. *Medicinal Chemistry and Chemical Biology*, John Wiley & Sons).

Preparations of varieties of chemical compounds that contain fluoro groups are challenging. For example, Olah and Prakash discovered a synthon for adding difluorinated methyl groups (Prakash, et al. *Angew. Chem. Int. Ed.* 2003, 42, 5216). A synthon-based approach, however, limits the scope of the starting materials and efficiency of a synthetic plan. Methods of the introduction of trifluoromethyl groups involve expensive or toxic reagents (Ichikawa, et al. *Chem. Lett.* 1981, 12, 1679-1680; (Boechat, et al. *Current org. Syn.* 2010, 403-413) or gaseous fluoroform (Folleas, et al. *Tetrahedron*, 2000, 56, 275-283). There is an ongoing need for synthetic methods for preparation of fluoro groups-containing compounds that can be compatible with a large scope of substrates and under mild reaction conditions.

SUMMARY OF THE INVENTION

In one aspect, the present invention provides a composition comprising a base and a compound of Formula (I)

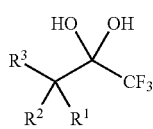

Formula (I)

wherein
$R^1$ is H, halo, or $C_{1-8}$ alkyl;
$R^2$ is H, halo, or $C_{1-8}$ alkyl; and
$R^3$ is H, halo, $C_{2-8}$ alkenyl, aryl, substituted aryl, substituted aryl, heteroaryl, substituted heteroaryl, $(CO)R^6$, $(CO)OR^6$, $(CO)SR^6$, $(CO)NR^6R^7$, $(SO_2)R^6$, $(PO)R^6R^7$, or $C(NR^6)R^7$, wherein $R^6$ and $R^7$ are independently selected from H, $C_{1-8}$ alkyl, O—$C_{1-5}$ alkyl, $C_{3-6}$ cycloalkyl, aryl-$C_{1-5}$ alkyl, heteroaryl-$C_{1-5}$ alkyl, aryl, substituted aryl, heteroaryl, and substituted heteroaryl;
or $R^2$ and $R^3$, together with the carbon atom to which they are attached, form a 4-7 membered cycloalkyl group or cyclo(hetero)alkyl group.

In another aspect, the present invention provides a salt comprising hexafluoroacetone hydrate and DBU. In some embodiments, the salt is anhydrous.

In another aspect, the present invention provides an anhydrous salt comprising hexafluoroacetone hydrate and DBU.

In a further aspect, the present invention provides a process for the modification of a chemical compound via the release of trifluoroacetate, the process comprising the step of (a) reacting the chemical compound with a composition comprising a base and a compound of Formula (I)

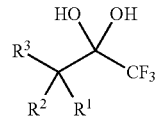

Formula (I)

wherein:
$R^1$ is H, halo, or $C_{1-8}$ alkyl;
$R^2$ is H, halo, or $C_{1-8}$ alkyl; and
$R^3$ is H, halo, $C_{2-8}$ alkenyl, aryl, substituted aryl, heteroaryl, substituted heteoaryl, $(CO)R^6$, $(CO)OR^6$, $(CO)SR^6$, $(CO)NR^6R^7$, $(SO_2)R^6$, $(PO)R^6R^7$, or $C(NR^6)R^7$, wherein $R^6$ and $R^7$ are independently selected from H, $C_{1-8}$ alkyl, O—$C_{1-5}$ alkyl, $C_{3-6}$ cycloalkyl, aryl-$C_{1-5}$ alkyl, and heteroaryl-$C_{1-5}$ alkyl, aryl, heteroaryl, and substituted heteroaryl;
or $R^2$ and $R^3$, together with the carbon atom to which they are attached, form a 4-7 membered cycloalkyl group or cyclo(hetero)alkyl group.

In some embodiments, the trifluoroacetate is released during the reaction. In other embodiments, the composition releases trifluoroacetate during the reaction.

In some embodiments, the composition is prepared by the process comprising the step of reacting the base with the compound of Formula (I) in a solvent to form the composition. In other embodiments, the composition is DBU/Hexafluoroacetone hydrate salt.

In some embodiments, the process comprises the step of adding the base to a solution comprising the chemical compound and the compound of Formula (I).

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention provides compositions that can be useful for the modification of chemical compounds via the release of trifluoroacetate.

In some embodiments, the compositions include a base and a compound of Formula (I)

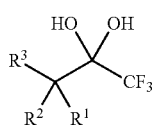

Formula (I)

in which

R¹ can be H, halo, or $C_{1-8}$ alkyl;

R² can be H, halo, or $C_{1-8}$ alkyl; and

R³ can be H, halo, $C_{2-8}$ alkenyl, aryl, substituted aryl, heteroaryl, substituted heteoaryl, $(CO)R^6$, $(CO)OR^6$, $(CO)SR^6$, $(CO)NR^6R^7$, $(SO_2)R^6$, $(PO)R^6R^7$, or $C(NR^6)R^7$, in which $R^6$ and $R^7$ are independently selected from H, $C_{1-8}$ alkyl, $O$—$C_{1-5}$ alkyl, $C_{3-6}$ cycloalkyl, aryl-$C_{1-5}$ alkyl, and heteroaryl-$C_{1-5}$ alkyl, aryl, substituted aryl, heteroaryl, and substituted heteoaryl;

or R² and R³, together with the carbon atom to which they are attached, can form a 4-7 membered cycloalkyl group or cyclo(hetero)alkyl group.

In some embodiments, the term "compound" is meant to include all stereoisomers, geometric isomers, tautomers, and isotopes of the structures depicted.

In some embodiments, $R^1$ can be H. In other embodiments, $R^1$ can be halo, for example, fluoro, or chloro, or bromo. In certain embodiments, $R^1$ can be fluoro.

In some embodiments, $R^2$ can be H. In some embodiments, $R^2$ can be halo, for example, fluoro, or chloro, or bromo. In certain embodiments, $R^2$ can be fluoro. In some embodiments, $R^2$ can be $C_{1-8}$ alkyl, for example, $CH_3$ or $CH_2CH_3$.

In some embodiments, $R^3$ can be H. In some embodiments, $R^3$ can be halo, for example, fluoro, or chloro, or bromo. In other embodiments, $R^3$ can be fluoro. In some embodiments, $R^3$ can be $C_{2-8}$ alkenyl, for example, $CH_2=CH_2$ or $CH_2=CHCH_3$. In some embodiments, $R^3$ can be aryl. In other embodiments, $R^3$ can be $C_{6-10}$ aryl, for example, phenyl or naphthalyl. In some embodiments, $R^3$ can be phenyl. In other embodiments, $R^3$ is substituted phenyl. In some embodiments, $R^3$ can be heteroaryl. In certain embodiments, $R^3$ can be heteroaryl having 5-10 ring atoms, for example, imidazole, or pyridine, or indole. In some embodiments, $R^3$ can be substituted heteroaryl having 5-10 ring atoms.

In some embodiments, $R^3$ can be $(CO)R^6$, for example, $(CO)CH_3$ or $(CO)C_2H_5$. In some embodiments, $R^3$ can be (CO)-phenyl.

In some embodiments, both $R^1$ and $R^2$ can be halo. In some embodiments, both $R^1$ and $R^2$ can be fluoro. In other embodiments, all of $R^1$, $R^2$, and $R^3$ can be halo. In some embodiments, all of $R^1$, $R^2$, and $R^3$ can be fluoro.

In some embodiments, the base can be an organic base. Suitable organic bases may include alkoxides (e.g., sodium ethoxide), linear aliphatic amines, and cyclic amines. In some embodiments, the organic base can be an amine compound. In some embodiments, the amine compound is a primary amine, for example, benzylamine. In other embodiments, the amine compound is a tertiary amine. In some embodiments, the tertiary amine compound can be TEA (triethylamin) or DIPEA (N,N-Diisopropylethylamine). In some embodiments, the base can be TEA. In other embodiments, the base can be DIPEA. In some embodiments, the base can be DBU (1,8-Diazabicyclo[5.4.0]undec-7-ene), or DABCO (1,4-diazabicyclo[2.2.2]octane), or DBN (1,5-Diazabicyclo[4.3.0] non-5-ene). In other embodiments, the base can be DMAP (4-Dimethylaminopyridine), morpholine, or (−)-sparteine. In certain embodiments, the base can be DBU. In other embodiments, the base can be inorganic bases. In some embodiments, the inorganic bases can be KOH, NaOH, or $NH_4OH$, and the like.

In some embodiments, the composition may be anhydrous. In some embodiments, the composition can be a salt. In certain embodiments, the composition can be an anhydrous salt.

In some embodiments, the compositions of the present invention can be prepared by the process comprising the step of reacting a base and a compound of Formula (I) in a solvent. In some embodiments, the base may be added to a solution of the compound of Formula (I). In other embodiments, the compound of Formula (I) can be added to a solution of the base, or any other methods known in the art. The solvent can be any solvents known in the art. Examples of suitable inert solvents include, but are not limited to, hydrocarbons, for example, hexane, petroleum ether, benzene, toluene, or xylene; chlorinated hydrocarbons, example, 1,2-dichloroethane, trifluoromethylbenzene, chloroform, or dichloromethane; alcohols, example, methanol, ethanol, isopropanol, n-propanol, n-butanol, or tert-butanol; ethers, example, diethyl ether ($Et_2O$), diisopropyl ether, tetrahydrofuran (THF), or dioxanee; glycol ethers, example, ethylene glycol monomethyl, or monoethyl ether, or ethylene glycol dimethyl ether (diglyme); ketones, example, acetone or butanone; amides, example, acetamide, dimethylacetamide, N-methyl-pyrrolidone (NMP), or dimethylformamide (DMF); nitrites, example, acetonitrile; sulfoxides, example, dimethyl sulfoxide (DMSO); nitro compounds, example, nitromethane, or nitrobenzene; esters, example, ethyl acetate, or mixtures of the said solvents. In some embodiments, the solvent can be THF, $Et_2O$, dioxane, or benzne. In some embodiments, the solvent can be THF. In other embodiments, the solvent can be dioxane. In some embodiments, the solvent can be $Et_2O$. In some embodiments, the solvent can be a mixture of THF and $Et_2O$, or a mixture of dioxane and $Et_2O$, or a mixture of DMF and THF, or a mixture of DMF and toluene.

In some embodiments, the composition of the present invention can be prepared at a temperature of from about −30° C. to about 60° C. In some embodiments, the composition can be prepared at a temperature of from about −20° C. to about 50° C. In other embodiments, the composition can be prepared at a temperature of from about −10° C. to about 50° C. In certain embodiments, the composition can be prepared at a temperature of from about 10° C. to about 40° C. In other embodiments, the composition can be prepared at a temperature of from about 10° C. to about 25° C. In certain embodiments, the composition can be prepared at a temperature of from about 20° C. to about 30° C. In certain embodiments, the composition can be prepared at room temperature.

The composition of the invention may be a solid. The solid form of the composition may be isolated and purified, for example, by filtration and washing, or by recrystallization. The collected composition can be further dried. The drying can be air drying, oven or vacuum drying. In other embodiments, the composition may be a liquid, which may be isolated by precipitation via adding an inert solvent to the formed composition.

The composition may release trifluoroacetate upon reacting with chemical compounds. In some embodiments, the release of trifluoroacetate is accompanied by the introduction of a trifluoromethyl group to the chemical compounds.

The present invention provides an anhydrous salt that includes hexafluoroacetone hydrate and DBU.

The present invention provides a salt that includes hexafluoroacetone hydrate and an organic base. In some embodiments, the organic base is an amine compound. In certain embodiments, the base is DBU. In other embodiments, the salt is anhydrous.

The present invention provides anhydrous salts that include hexafluoroacetone hydrate and a base. In some embodiments, the base can be an organic base. In other embodiments, the base can be DBU. In certain embodiments, the present invention provides anhydrous salts that include hexafluoroacetone hydrate and DBU. In some embodiments, the DBU/Hexafluoroacetone hydrate salt may include a 1:1 molar ratio of DBU to hexafluoroacetone hydrate.

Hexafluoroacetone trihydrate and DBU (1,8-Diazabicyclo[5.4.0]undec-7-ene) are commercially available. For example, hexafluoroacetone trihydrate can be purchased from SynQuest Labs, and DBU can be purchased from Aldrich.

The DBU/Hexafluoroacetone hydrate salt can be prepared by any methods known in the art for the generation of a salt, for example, by reacting DBU and Hexafluoroacetone hydrate in a solvent. In some embodiments, DBU can be added to a solution of Hexafluoroacetone hydrate. In other embodiments, Hexafluoroacetone hydrate can be added to a solution of DBU. The solvent can be any organic solvents known in the art. Examples of suitable organic solvents include, but are not limited to, hydrocarbons, for example, hexane, petroleum ether, benzene, toluene, or xylene; chlorinated hydrocarbons, for example, 1,2-dichloroethane, trifluoromethylbenzene, chloroform, or dichloromethane; alcohols, for example, methanol, ethanol, isopropanol, n-propanol, n-butanol, or tert-butanol; ethers, for example, diethyl ether, diisopropyl ether, tetrahydrofuran (THF), or dioxanee; glycol ethers, for example, ethylene glycol monomethyl or monoethyl ether, or ethylene glycol dimethyl ether (diglyme); ketones, for example, acetone, or butanone; amides, for example, acetamide, dimethylacetamide, N-methyl-pyrrolidone (NMP), or dimethylformamide (DMF); nitriles, for example, acetonitrile; sulfoxides, for example, dimethyl sulfoxide (DMSO); nitro compounds, for example, nitromethane, or nitrobenzene; esters, for example, ethyl acetate, or mixtures of the said solvents.

In some embodiments, the solvent can be THF, $Et_2O$, dioxane, or benzne. In some embodiments, the solvent can be THF. In other embodiments, the solvent can be dioxane. In some embodiments, the solvent can be $Et_2O$. In some embodiments, the solvent can be a mixture of THF and $Et_2O$, or a mixture of dioxane and $Et_2O$, or a mixture of DMF and THF, or a mixture of DMF and toluene. In other embodiments, the DBU/Hexafluoroacetone hydrate salt can be prepared by mixing DBU and Hexafluoroacetone hydrate in a first solvent, followed by addition of a second solvent in order to precipitate the DBU/Hexafluoroacetone hydrate salt from the first solvent.

In some embodiments, the DBU/Hexafluoroacetone hydrate salt can be prepared at a temperature of from about −30° C. to about 60° C. In some embodiments, the DBU/Hexafluoroacetone hydrate salt can be prepared at a temperature of from about −20° C. to about 50° C. In some embodiments, the DBU/Hexafluoroacetone hydrate salt can be prepared at a to temperature of from about −10° C. to about 50° C. In other embodiments, the DBU/Hexafluoroacetone hydrate salt can be prepared at a temperature of from about 0° C. to about 40° C. In certain embodiments, the DBU/Hexafluoroacetone hydrate salt can be prepared at a temperature of from about 10° C. to about 40° C. In some embodiments, the DBU/Hexafluoroacetone hydrate salt can be prepared at a temperature of from about 10° C. to about 30° C. In other embodiments, the DBU/Hexafluoroacetone hydrate salt can be prepared at a temperature of from about 10° C. to about 25° C. In some embodiments, the DBU/Hexafluoroacetone hydrate salt can be prepared at a temperature of from about 15° C. to about 25° C. In other embodiments, the DBU/Hexafluoroacetone hydrate salt can be prepared at a temperature of from about 20° C. to about 25° C. In certain embodiments, the DBU/Hexafluoroacetone hydrate salt can be prepared at a temperature of from about 20° C. to about 30° C. In some embodiments, the DBU/Hexafluoroacetone hydrate salt can be prepared at a temperature of from about 25° C. to about 30° C. In certain embodiments, the DBU/hexafluoroacetone hydrate salt can be prepared at room temperature.

The DBU/Hexafluoroacetone hydrate salt, in some embodiments, is a white solid. It can be referred to a solid form of trifluoromethyl anion (fluoroform). Thus, it can be easily accessible or handled in the application of the salt. The DBU/Hexafluoroacetone hydrate salt can be fully soluble in many organic solvents, for example, DMSO, DMF, $CH_3CN$, EtOAc, $CH_2Cl_2$, and $CHCl_3$. The DBU/Hexafluoroacetone hydrate salt can be partly soluble in toluene and THF.

The DBU/Hexafluoroacetone hydrate salt may release trifluoroacetate upon reacting with chemical compounds. In some embodiments, the release of trifluoroacetate is accompanied by the introduction of a trifluoromethyl group to the chemical compounds.

The present invention provides a process of using a composition of the present invention for the modification of a chemical compound via the release of trifluoroacetate, the process including the steps of (a) reacting the chemical compound with a composition comprising a base and a compound of Formula (I)

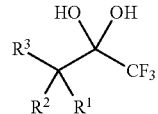

Formula (I)

in which
$R^1$ can be H, halo, or $C_{1-8}$ alkyl;
$R^2$ can be H, halo, or $C_{1-8}$ alkyl; and
$R^3$ can be H, halo, $C_{2-8}$ alkenyl, aryl, substituted aryl, heteroaryl, substituted heteroaryl, $(CO)R^6$, $(CO)OR^6$, $(CO)SR^6$, $(CO)NR^6R^7$, $(SO_2)R^6$, $(PO)R^6R^7$, or $C(NR^6)R^7$, in which $R^6$ and $R^7$ can be independently selected from H, $C_{1-8}$ alkyl, O—$C_{1-5}$ alkyl, $C_{3-6}$ cycloalkyl, aryl-$C_{1-5}$ alkyl, heteroaryl-$C_{1-5}$ alkyl, aryl, substituted aryl, heteroaryl, and substituted heteroaryl;

or $R^2$ and $R^3$, together with the carbon atom to which they are attached, can form a 4-7 membered cycloalkyl group or cyclo(hetero)alkyl group.

In some embodiments, the trifluoroacetate can be released during the reaction. In other embodiments, the composition may release trifluoroacetate.

In some embodiments, the composition can be prepared by the process including the step of reacting the base with a compound of Formula (I) in a solvent to form the composition. In other embodiments, the composition can be a salt of the base and the compound of Formula (I). In some embodiments, the base can be an organic base. In certain embodiments, the base can be DBU. In other embodiments, the solvent can be diethyl ether. In some embodiments, the composition can be the DBU/Hexafluoroacetone hydrate salt.

In some embodiments, the term "reacting" is meant to refer to the bringing together of the indicated reagents in such a way as to allow their molecular interaction and chemical transformation according to the thermodynamics and kinetics of the chemical system. In other embodiments, reacting can be facilitated, particularly for solid reagents, by using an appropriate solvent or mixture of solvents in which at least one of the reagents is at least partially soluble. Reacting is typically carried out for a suitable time and under conditions suitable to bring about the desired chemical transformation.

In some embodiments, the base can be an organic base. In other embodiments, the base can be DBU and the compound of Formula (I) can be hexafluoroacetone hydrate.

In some embodiments, the chemical compound can be an aldehyde or a ketone. In some embodiments, the chemical compound can be alkyl aldehyde. In other embodiments, the chemical compound can be an aryl aldehyde. In some embodiments, the chemical compound can be a heteroaryl aldehyde. In other embodiments, the chemical compound can be dialkylketone. In other embodiments, the chemical compound can be diarylketone. In certain embodiments, the chemical compound can be aryl alkylketone. In some embodiments, the chemical compounds can be diheteroarylketone. In certain embodiments, the chemical compound can be heteroaryl alkylketone.

In some embodiments, the chemical compounds may undergo a trifluoromethylation reaction.

In some embodiments, the process can comprise the step of adding the base to a solution comprising the chemical compound to be modified and the compound of Formula (I). In some embodiments, the chemical compound can be an aldehyde, for example, an aryl aldehyde. In other embodiments, the chemical compound can be an alkyl aldehyde.

In some embodiments, the base can be organic bases. Suitable organic bases may include alkoxides (e.g., sodium ethoxide), linear aliphatic amines, and cyclic amines. In some embodiments, the organic base can be an amine compound. In some embodiments, the amine compound is a primary amine. In other embodiments, the amine compound is a tertiary amine. In some embodiments, the tertiary amine compound can be triethylamine (TEA). In other embodiments, the base can be inorganic bases, for example, KOH, NaOH, or $NH_4OH$, and the like.

In some embodiments, the base can be triethylamine. In other embodiments, the compound of Formula (I) can be a compound of Formula (III)

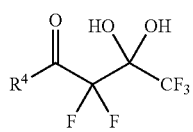

Formula (III)

in which
R$^4$ can be R$^6$, OR$^6$, SR$^6$, or NR$^6$R$^7$, in which R$^6$ and R$^7$ can be independently selected from H, $C_{1-8}$ alkyl, O—$C_{1-5}$ alkyl, $C_{3-6}$ cycloalkyl, aryl-$C_{1-5}$ alkyl, and heteroaryl-$C_{1-5}$ alkyl, aryl, substituted aryl, heteroaryl, and substituted heteroaryl.

In some embodiment, the solution may include a salt, for example, a metal halide. In some embodiments, the metal halide is LiBr.

In some embodiments, the DBU/Hexafluoroacetone hydrate salt can be used to modify chemical compounds for introduction of a desired functional group via the release of trifluoroacetate. For example, the salt can be used for the trifluoromethylation of chemical compounds, thus, introducing a trifluoromethyl group to the chemical compounds. In some embodiments, the DBU/Hexafluoroacetone hydrate salt can be used to add a trifluoromethyl group to chemical compounds, for example, carbonyl compounds, as shown in Scheme 1, wherein each of R$^p$ and R$^q$ can be independently H, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which can be optionally substituted.

Scheme 1

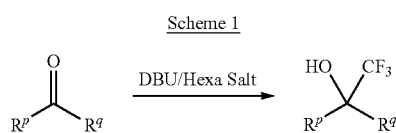

The chemical compounds that can be trifluoromethylated include, but are not limited to, aldehydes and ketones. In some embodiments, the aldehydes can be aryl aldehydes. In some embodiments, the aldehydes can be alkyl aldehydes. In some embodiments, the aryl aldehydes can be benzaldehyde or substituted benzaldehyde. In some embodiments, the ketones can be diarylketones, or alkylaryl ketones, or dialkylketones.

In some embodiments, the trifluoromethylation of chemical compounds by the DBU/Hexafluoroacetone hydrate salt may require the presence of a base to speed up the reaction. The base can be KHMDS, or KH, or Dimsyl-K, or t-BuOK. In some embodiments, the base can be KHMDS. In other embodiments, the base can be t-BuOK. In some embodiments, the modification of chemical compounds by the DBU/Hexafluoroacetone hydrate salt may require about 1 equivalent of the base, or about 2 equivalents of the base, or about 3 equivalents of the base, or about 4 equivalents of the additional base, or about 5 equivalents of the base, or about 6 equivalents of the base. In other embodiments, the modification of chemical compounds by the DBU/Hexafluoroacetone hydrate salt may require about 4 equivalents of the base, or about 5 equivalents of the base.

In some embodiments, the trifluoromethylation of chemical compounds by the DBU/Hexafluoroacetone hydrate salt may require the presence of an additive. The additive can be any one known in the art that is suitable for trifluoromethylation. The additive can be crown ether, for example, 18-crown-6. In some embodiments, the additive can be a quaternary ammonium salt, for example, $Bu_4N^+Cl^-$ or $Bu_4N^+Br^-$. The amount of the additive can be from about 1 equivalent to about 6 equivalents. In some embodiments, the amount of the additive can be from about 2 equivalents to about 5 equivalents. In some embodiments, the amount of the additive can be from about 1.5 equivalents to about 5 equivalents. In other embodiments, the amount of the additives can be from about 2 equivalents to about 3 equivalents. In certain embodiments, the amount of the additive can be from about 2.5 equivalents to about 3.5 equivalents. In some embodiments, the amount of the additive can be from about 2.5 equivalents to about 4.5 equivalents. In certain embodiments, the amount of the additive can be from about 3 equivalents to about 4.5 equivalents. In some embodiments, the amount of the additive can be from about 3.5 equivalents to about 4.5 equivalents. In other embodiments, the amount of the additive is the same equivalent as the amount of the base required for a trifluoromethylation reaction. In certain embodiments, trifluoromethylation by the DBU/Hexafluoroacetone hydrate salt may not need the presence of an additive.

In a trifluoromethylation reaction, the DBU/Hexafluoroacetone hydrate salt can form fluoroform upon heating to 50° C. for four hours or upon the addition of a base. This transformation may be quantitative and can be observed by $^{19}$F NMR as both the signals for trifluoroacetate and fluoroform can be seen. In some embodiments, the trifluoromethylation reaction may require about 1 equivalent of the DBU/Hexafluoroacetone hydrate salt. In other embodiments, the trifluoromethylation may require about 2 equivalents of the DBU/Hexafluoroacetone hydrate salt. In certain embodiments, the trifluoromethylation reaction may require about 1.5 equivalents of the DBU/Hexafluoroacetone hydrate salt. In some embodiments, the trifluoromethylation reaction may require about 1.25 equivalents of the DBU/Hexafluoroacetone hydrate salt. In certain embodiments, the trifluoromethyaltion reaction may require about 1.75 equivalents of the DBU/Hexafluoroacetone hydrate salt.

In some embodiments, the trifluoromethylation reaction by the DBU/Hexafluoroacetone to hydrate salt via the release of trifluoroacetate can be achieved at a temperature of from about −78° C. to about 0° C. In some embodiments, the trifluoromethylation reaction can be conducted at a temperature of from about −78° C. to about −30° C. In other embodiments, the trifluoromethylation reaction can be conducted at a temperature of from about −50° C. to about −30° C. In some embodiments, the trifluoromethylation reaction can be conducted at a temperature of from about −30° C. to about 0° C. In certain embodiments, the trifluoromethylation reaction can be conducted at a temperature of from about −25° C. to about 0° C. In other embodiments, the trifluoromethylation reaction can be conducted at a temperature of from about −25° C. to about −10° C. In some embodiments, the trifluoromethylation reaction can be conducted at a temperature of from about −20° C. to about −10° C. In certain embodiments, the trifluoromethylation reaction can be conducted at a temperature of from about −15° C. to about 0° C. In some embodiments, the trifluoromethylation reaction can be conducted at a temperature of from about −10° C. to about 0° C. In some embodiments, the trifluoromethylation reaction can be conducted at a temperature of from about 0° C. to about 60° C. In other embodiments, the trifluoromethylation reaction can be conducted at a temperature of from about 5° C. to about 50° C. In other embodiments, the trifluoromethylation reaction can be conducted at a temperature of from about 5° C. to about 40° C. In certain embodiments, the trifluoromethylation reaction can be conducted at a temperature of from about 10° C. to about 40° C. In other embodiments, the trifluoromethylation reaction can be conducted at a temperature of from about 10° C. to about 30° C. In some embodiments, the trifluoromethylation reaction can be conducted at a temperature of from about 20° C. to about 30° C. In certain embodiments, the trifluoromethylation reaction can be conducted at a temperature of from about 10° C. to about 25° C. In some embodiments, the trifluoromethylation reaction can be conducted at a temperature of from about −30° C. to about 30° C. In other embodiments, the trifluoromethyaltion reaction can be conducted at a temperature of from about −30° C. to about 25° C. In certain embodiments, the trifluoromethylation reaction can be conducted at a temperature of from about −30° C. to room temperature.

In some embodiments, chemical compounds can undergo an olefination reaction via the release of trifluoroacetate. In certain embodiments, chemical compounds may undergo a trifluoroacetylative olefination reaction as shown in Scheme 2, wherein each of R$^m$ and R$^n$ can be independently H, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which can be optionally substituted.

Scheme 2

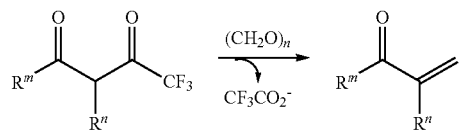

In some embodiments, the olefination reaction may be an α-methylenation reaction.

The chemical compounds that can undergo an α-methylenation reaction via the release of trifluoroacetate may contain a moiety of 4,4,4-trifluoromethyl-1,3-butanedione. Some 4,4,4-trifluoromethyl-1,3-butanedione-containing compounds are commercially available. Others can be prepared by Danheiser's protocol for an efficient trifluoroacetylation with LiHMDS and CF$_3$CO$_2$CH$_2$CF$_3$ (Danheiser, et al. *J. Org. Chem.* 1990, 55, 1959-1964).

4,4,4-trifluoromethyl-1,3-butanedione-containing compounds may be converted to the respective olefins in excellent yields. Suitable bases for the conversion can be any organic bases and inorganic bases known in the art. In some embodiments, the base can be an inorganic base, for example, K$_2$CO$_3$ or Na$_2$CO$_3$. In certain embodiments, the base can be K$_2$CO$_3$. In other embodiments, the base can be an organic base, for example, TEA or DIPEA (N,N-Diisopropylethylamine). In some embodiments, inorganic bases, for example, K$_2$CO$_3$, may be easily removed by aqueous workup.

Suitable solvent for the methylenation can be any organic solvents known in the art. In some embodiments, the solvent can be benzene, toluene, or xylene. In some embodiments, the methylenation reaction may be achieved at a temperature of from about 0° C. to about 100° C. In some embodiments, the temperature can be from about 25° C. to about 100° C. In other embodiments, the temperature can be from about 25° C. to about 80° C. In some embodiments, the temperature can be from about 50° C. to about 80° C. In certain embodiments, the temperature can be from about 50° C. to about 70° C. In other embodiments, the temperature can be from about 50° C. to about 60° C.

The olefination strategy through trifluoroacetate release can be applied to an array of ketones, lactams, and lactones. For chemical compounds that do not contain a 4,4,4-trifluoromethyl-1,3-butanedione moiety, the compounds may undergo a two-step detrifluoroacetylative olefination as shown in Scheme 3, wherein R$^m$ and R$^n$ can be independently H, alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which can be optionally substituted.

Scheme 3

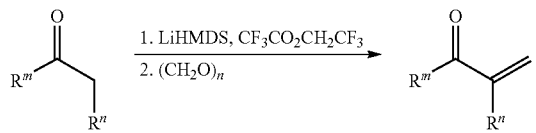

The chemical compounds may undergo an efficient trifluoroacetylation with LiHMDS and CF$_3$CO$_2$CH$_2$CF$_3$ to afford trifluoroacetylated intermediates. The unpurified trifluoroacetylated intermediates may be immediately subjected to olefination by trifluoroacetate release to give corresponding enones. For chemical compounds having steric bulk at the positions neighboring the α-carbon, the formation of olefin products is significant in the synthetic chemistry. The olefination reactions thus demonstrate a mild reaction conditions through trifluoroacetate release. Further, the olefination reaction avoids the use of toxic selenium reagents, which are a common choice for synthesizing vinyl ketones. For highly reactive ketones, the use of harsh oxidants such as chromium also can be avoided.

The olefination reaction via trifluoroacetate release of the present invention can be applied to the synthesis of complex natural products, as shown in Examples 37 and 39-41.

In some embodiments, the trifluoroacetate release strategy can be applied to the cleavage of a C—C bond, thus generating α,α-difluoroenolates for aldol reactions as shown in Scheme 4, wherein variable $R^4$ can be independently defined anywhere herein.

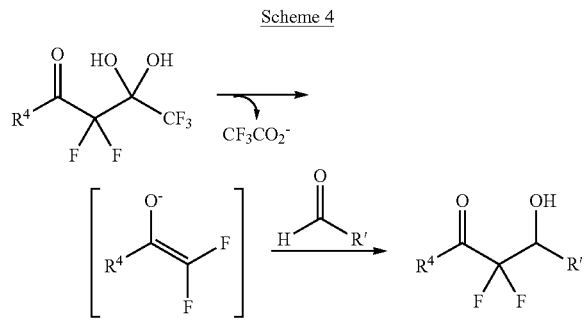

Scheme 4

The starting materials, gem-diols, can be easily prepared under neutral conditions using Selectfluor and 1,1,1-trifluoro-2,4-dione containing compounds. Some 1,1,1-trifluoro-2,4-diones are commercially available, and others are readily accessed by trifluoromethylation of methyl ketones. In some embodiments, 1,1,1-trifluoro-2,4-diones can exist exclusively in the enol form.

In some embodiments, trifluoroacetate release can be promoted rapidly in the presence of a base. In some embodiments, the bases can be an organic base or an inorganic base as described herein. In some embodiments, the base can be an organic base. In some embodiments, the organic base can be an amine, for example, a tertiary amine compound. The tertiary amine compound can be triethylamine or DIPEA. In some embodiments, the base is triethylamine. In other embodiments, the trifluoroaceate release may require the presence of a salt. In some embodiments, the salt can be metal halides, for example, Lithium halides. In other embodiments, the salt can be lithium bromide.

In some embodiments, the solvent suitable for successful release of trifluoroacetate can be any organic solvents known in the art. Examples of suitable organic solvents include, but are not limited to, hydrocarbons, for example, hexane, petroleum ether, benzene, toluene, or xylene; chlorinated hydrocarbons, for example, 1,2-dichloroethane, trifluoromethylbenzene, chloroform, or dichloromethane; alcohols, for example, methanol, ethanol, isopropanol, n-propanol, n-butanol, or tert-butanol; ethers, for example, diethyl ether, diisopropyl ether, tetrahydrofuran (THF), or dioxanee; glycol ethers, for example, ethylene glycol monomethyl or monoethyl ether, or ethylene glycol dimethyl ether (diglyme); ketones, for example, acetone, or butanone; amides, for example, acetamide, dimethylacetamide, N-methyl-pyrrolidone (NMP), or dimethylformamide (DMF); nitrites, for example, acetonitrile; sulfoxiddes, for example, dimethyl sulfoxide (DMSO); nitro compounds, for example, nitromethane, or nitrobenzene; esters, for example, ethyl acetate, or mixtures of the said solvents.

The difluoroenolate may react with electrophiles, for example, an aldehyde or a ketone. The aldehyde or ketone can be any aldehydes or ketones known in the art. The aldehyde can be an alkyl aldehyde or an aryl aldehyde. In some embodiments, the aldehyde can be α,β-unsaturated aldehyde.

In some embodiments, the difluoroenolate can react with electrophiles to undergo an to aldol reaction. In some embodiments, the reaction may be completed at a temperature of from about −78° C. to about 25° C. In some embodiments, the reaction can be completed at a temperature of from about −50° C. to about 25° C. In other embodiments, the reaction can be completed at a temperature of from about −30° C. to about 25° C. In certain embodiments, the reaction can be completed at a temperature of from about −10° C. to about 25° C. In some embodiments, the reaction can be completed at a temperature of from about −78° C. to about −50° C. In other embodiments, the reaction can be completed at a temperature of from about −50° C. to about −30° C. In certain embodiments, the reaction can be completed at a temperature of from about −30° C. to about −10° C. In some embodiments, the reaction can be completed at a temperature of from about 25° C. to about 100° C. In certain embodiments, the reaction can be completed at a temperature of from about 25° C. to about 80° C. In other embodiments, the reaction can be completed at a temperature of from about 25° C. to about 60° C. In other embodiments, the reaction can be completed at a temperature of from about 25° C. to about 40° C.

In some embodiments, the reaction condition can be very mild. In some embodiments, the reaction may take about 3 minutes to about 30 minutes. In some embodiments, the reaction may take about 3 minutes to about 20 minutes. In other embodiments, the reaction may take about 3 minutes to about 10 minutes.

In other embodiments, the present invention provides a process for synthesis of fluoro-containing compounds that are useful for the preparation of molecules that have utility as probes in drug metabolism studies, for example, $^{19}$F-NMR based drug metabolism studies.

In some embodiments, the present invention provides a trifluoroacetate-release strategy that can be adapted to generate α,α-difluoroenolates. In some embodiments, this strategy comprises replacing one fluorine atom on hexafluoroacetone hydrate with a group that stabilizes an anion, such as a carbonyl group as an enolate. In other embodiments, this replacement of one fluorine atom on hexafluoroacetone hydrate with a carbonyl group stabilizes the anion as an enolate.

In some embodiments, the present invention provides a method of employing a trifluoroacetate-release strategy to generate reactive intermediates, for example, α,α-difluoroenolates. In other embodiments, this strategy can prepare α,α-difluoroenolates using reaction conditions that may be exceedingly mild.

In some embodiments, the trifluoroacetate-release strategy may be readily adapted to generate enolates other than α,α-difluoroenolates. For example, the enolates other than α,α-difluoroenolates may be α-mono-haloenolates, such as α-bromoenolates, and the like.

The present invention provides, in some embodiments, a process for preparing halo-containing compounds, for example, fluorine-containing compounds. In some embodiments, the process can utilize the release of trifluoroacetate as a mild and efficient way for preparation of reactive intermediates that are very difficult to prepare using existing methods. In some embodiments, the trifluoroacetate release process can be useful for versatile generation of difluoroenolates.

In some embodiments, the trifluoroacetate release process can be applicable in various chemical processes, for example, chemical processes that comprise aldol and imino-aldol reactions. In other embodiments, the trifluoroacetate release process can be applied in imino-aldol reactions to provide products comprising difluorinated beta-amino acids that may be important building blocks for the preparation of biopolymers for drug discovery.

In some embodiments, the present invention provides a process for preparation of fluoro-containing compounds. In some embodiments, the process can be useful as building blocks that have utility in drug discovery. In other embodiments, the process can be useful for the preparation of medicinally important molecules with increased bioavailability. Illustrative of the increased bioavailability is enhanced metabolic stability, increased lipophilicity, enhanced membrane permeability, and increased binding affinity. In other embodiments, the process can be useful for the preparation of molecules that have utility as probes in drug metabolism studies. Illustrative of the drug metabolism studies are $^{19}$F-NMR based drug metabolism studies.

In some embodiments, the present invention provides a process for preparing a fluoro-containing compound, the process comprising the step of preparing an intermediate via the release of trifluoroacetate. In other embodiments, the process further can comprise the step of adding a base. In certain embodiments, the base can be a tertiary amine, for example, triethylamine. In other embodiments, the process further can comprise the step of adding a salt. The salt can be a metal halide, for example, LiBr.

In other embodiments, the present invention provides a process for preparing a fluoro-containing compound, the process comprising the step of preparing an intermediate via the release of trifluoroacetate, in which the intermediate can be a difluoroenolate. In other embodiments, the process further can comprise the step of trifluoroacetylation of a corresponding methyl ketone. In other embodiments, the process further can comprise the step of fluorinating an acyl trifluoroacetone with a fluorinating agent. For example, the fluorinating agent can be an N-fluoro tertiary amine, and the like.

In other embodiments, the process further can comprise the step of performing an aldol reaction. In other embodiments, the process further can comprise the step of performing an imino-aldol reaction, and similar reactions.

In some embodiments, the fluoro-containing compound can be a difluoro beta-amino acid. For example, the fluoro-containing compound can be a fluorinated biopolymer, or a difluoro analog of an ether, or a difluoro analog of a phosphate, phosphonate, or phosphinate, or a difluoro analog of a drug. In some embodiments, the difluoro group can replace a metabolically active methylene group.

In other embodiments, the present invention provides a process for preparing a fluoroketone, the process comprising the steps of: (a) reacting the corresponding ketone with a trifluoroacetylating agent; (b) reacting the trifluoroacetylated ketone with a fluorinating agent; and (c) reacting the fluorinated trifluoroacetylated ketone with a base.

In other embodiments, the present invention provides a process for preparing an alpha-unsaturated fluoro compound, the process comprising the steps of: (a) reacting the corresponding alpha-unsaturated compound with a trifluoroacetylating agent; (b) reacting the trifluoroacetylated compound with a fluorinating agent; and (c) reacting the fluorinated trifluoroacetylated compound with a base. In other embodiments, the corresponding alpha-unsaturated compound can be a ketone, or an ester, or a thioester, or a dithioester, or an amide, or an oxime, or a hydrazone, or a sulfoxide, or a sulfone, or a phosphate, or a phosphonate, or a phosphinate, or an alkene, or an arene, or a heteroarene, all of which are optionally substituted, and the like.

In other embodiments, the present invention provides a process for preparing a halo-containing compound, the process comprising the step of preparing an intermediate via the release of trifluoroacetate. In other embodiments, the process further can comprise the step of adding a base. In some embodiments, the base can be a tertiary amine. In other embodiments, the process further can comprise the step of adding a salt. In some embodiments, the salt can be a metal halide. In some embodiments, the intermediate can be a haloenolate. In some embodiments, the process further can comprise the step of trifluoroacetylation of the corresponding methyl ketone. In other embodiments, the process further can comprise the step of fluorinating an acyl trifluoroacetone with a fluorinating agent. For example, the fluorinating agent can be an N-fluoro tertiary amine.

In other embodiments, the process further can comprise the step of brominating an acyl trifluoroacetone with a brominating agent. In some embodiments, the brominating agent is a Br$^+$ donor.

In some embodiments, the process further can comprise the step of performing an aldol reaction. In certain embodiments, the aldol reaction can be an imino-aldol reaction.

In other embodiments, the halo-containing compound can be a difluoro beta-amino acid. In other embodiments, the halo-containing compound can be a fluorinated biopolymer. In other embodiments, w the halo-containing compound can be a difluoro analog of an ether. In other embodiments, the halo-containing compound can be a difluoro analog of a phosphate, phosphonate, or phosphinate. In other embodiments, the halo-containing compound can be a difluoro analog of a drug, where the difluoro group may replace a metabolically active methylene group.

In other embodiments, the present invention provides a process for preparing a haloketone, the process comprising the steps of (a) reacting the corresponding ketone with a trifluoroacetylating agent; (b) reacting the trifluoroacetylated ketone with a halogenating agent; and (c) reacting the halogenated trifluoroacetylated ketone with a base.

In other embodiments, the present invention provides a process for preparing an alpha unsaturated halo compound, the process comprising the steps of (a) reacting the corresponding alpha unsaturated compound with a trifluoroacetylating agent; (b) reacting the trifluoroacetylated compound with a halogenating agent; and (c) reacting the halogenated trifluoroacetylated compound with a base.

In some embodiments, the alpha unsaturated compound can be a ketone. In some embodiments, the alpha unsaturated compound can be an ester. In some embodiments, the alpha unsaturated compound can be a thioester. In some embodiments, the alpha unsaturated compound can be a dithioester. In some embodiments, the alpha unsaturated compound can be an amide. In some embodiments, the alpha unsaturated compound can be an oxime. In some embodiments, the alpha unsaturated compound can be a hydrazone. In some embodiments, the alpha unsaturated compound can be a sulfoxide or a sulfone. In some embodiments, the alpha unsaturated compound can be a phosphate, phosphonate, or phosphinate. In some embodiments, the alpha unsaturated compound can be an optionally substituted alkene, arene, or heteroarene.

In some embodiments, the present invention provides a process for adding a functional group alpha to a ketone, the process comprising the steps of (a) reacting the corresponding ketone with a trifluoroacetylating agent; and (b) reacting the trifluoroacetylated ketone with an electrophilic precursor of the functional group.

In some embodiments, the process further can comprise the step of adding an additional functional group to the ketone, the step comprising adding a base and an electrophilic precursor of the additional functional group.

In some embodiments, the functional group can be halo. In other embodiments, the functional group can be fluoro or bromo. In some embodiments, the additional functional group can be an optionally substituted carbon. In certain embodiments, the additional functional group can be an alcohol. In some embodiments, the functional group and the additional functional group can be taken together to form an epoxide.

In some embodiments, the base can be a tertiary amine.

In some embodiments, the process further can comprise the step of adding a salt. In certain embodiments, the salt can be a metal halide.

In some embodiments, the electrophilic precursor of the functional group can be an N-fluoro tertiary amine. In some embodiments, the electrophilic precursor of the functional group can be a brominating agent. In some embodiments, the electrophilic precursor of the additional functional group can be an aldehyde. In some embodiments, the electrophilic precursor of the additional functional group can be an imine.

In some embodiments, the present invention provides a process for preparing an enolate, the process comprising the step of reacting a compound of the formula

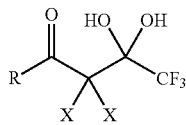

with a base; in which R can be alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which can be optionally substituted; and each X can be independently hydrogen or halo, or alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which can be optionally substituted; providing that both X cannot be hydrogen. In some embodiments, the base can be a tertiary amine.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

In some embodiments, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

In some embodiments, the term "alkenyl" refers to an alkyl group having one or more double carbon-carbon bonds. Example alkenyl groups include ethenyl, propenyl, and the like.

In some embodiments, the term "alkynyl" refers to an alkyl group having one or more triple carbon-carbon bonds. Example alkynyl groups include ethynyl, propynyl, and the like.

In some embodiments, the term "aryl" refers to monocyclic or polycyclic (e.g., having 2, 3 or 4 fused rings) aromatic hydrocarbons, for example, phenyl, naphthyl, anthracenyl, phenanthrenyl, and the like. In some embodiments, an aryl group has from 6 to about 20 carbon atoms.

In some embodiments, the term "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl to are moieties that have one or more aromatic rings fused (i.e., having a bond in common with) to the cycloalkyl ring, for example, benzo derivatives of cyclopentane, cyclopentene, cyclohexane, and the like. In some embodiments, a cycloalkyl group having one or more fused aromatic rings can be attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

In some embodiments, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

In some embodiments, "cycloheteroalkyl" refers to a non-aromatic heterocycle where one or more of the ring-forming atoms is a heteroatom such as an O, N, or S atom. Cycloheteroalkyl groups can include mono- or polycyclic (e.g., having 2, 3 or 4 fused rings) ring systems as well as spirocycles. Example cycloheteroalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of cycloheteroalkyl are moieties that have one or more aromatic rings fused (i.e., having a bond in common with) to the non-aromatic heterocyclic ring, for example phthalimidyl, naphthalimidyl, and benzo derivatives of heterocycles. In some embodiments, a cycloheteroalkyl group having one or more fused aromatic rings can be attached though either the aromatic or non-aromatic portion. Also included in the definition of cycloheteroalkyl are moieties where one or more ring-forming atoms is substituted by 1 or 2 oxo or sulfido groups. In some embodiments, the cycloheteroalkyl group has from 1 to about 20 carbon atoms, and in further embodiments from about 3 to about 20 carbon atoms. In some embodiments, the cycloheteroalkyl group contains 3 to about 20, 3 to about 14, 3 to about 7, or 5 to 6 ring-forming atoms. In some embodiments, the cycloheteroalkyl group has 1 to about 4, 1 to about 3, or 1 to 2 heteroatoms. In some embodiments, the cycloheteroalkyl group contains 0 to 3 double bonds. In some embodiments, the cycloheteroalkyl group contains 0 to 2 triple bonds.

In some embodiments, the term "halo" or "halogen" includes fluoro, chloro, bromo, and iodo.

In some embodiments, the term "alkoxy" refers to an —O-alkyl group. Example alkoxy groups include methoxy, ethoxy, propoxy (e.g., n-propoxy and isopropoxy), t-butoxy, and the like.

In some embodiments, the term "substituted" refers to the replacement of a hydrogen moiety with a non-hydrogen moiety in a molecule or group. The term "polysubstituted" means substituted with more than one substituent up to the valence of the substituted group. For example, a polysubstituted group can be substituted with 2, 3, 4, or 5 substituents. Generally when a list of possible substituents is provided, the substituents can be independently selected from that group.

In some embodiments, the term "amino" or "amine" includes the group $NH_2$, alkylamino, and dialkylamino, where the two alkyl groups in dialkylamino may be the same or different, i.e. alkylalkylamino. For example, amino includes methylamino, ethylamino, dimethylamino, methylethylamino, and the like. In addition, it is to be understood that when amino modifies or is modified by another term, such as aminoalkyl, or acylamino, the above variations of the term amino are included therein. For example, aminoalkyl includes $H_2N$-alkyl, methylaminoalkyl, ethylaminoalkyl, dimethylaminoalkyl, methylethylaminoalkyl, and the like. For example, acylamino includes acylmethylamino, acylethylamino, and the like.

In some embodiments, the term "optionally substituted" includes the replacement of hydrogen atoms with other functional groups on the radical that is optionally substituted. Such other functional groups For example include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. For example, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

In some embodiments, the terms "substituted aryl" and "substituted heteroaryl" include the replacement of hydrogen atoms with other functional groups on the aryl or heteroaryl.

Such other functional groups include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. For example, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted. Illustrative substituents include, but are not limited to, a radical —$(CH_2)_xZ^x$, where x is an integer from 0-6 and $Z^x$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl) aminoalkyl, alkylcarbonylaminoalkyl, N—($C_1$-$C_6$ alkyl) alkylcarbonylaminoalkyl, cyano, and nitro; or $Z^x$ is selected from —$CO_2R^a$ and —$CONR^bR^c$, where $R^a$, $R^b$, and $R^c$ are each independently selected in each occurrence from hydrogen, $C_1$-$C_6$ alkyl, aryl-$C_1$-$C_6$ alkyl, and heteroaryl-$C_1$-$C_6$ alkyl.

EXAMPLES

The following examples further illustrate specific embodiments of the invention; however, the following examples should not be interpreted in any way to limit the invention.

Example 1

1,1,1-Trifluoro-2,4-diones

The 1,1,1-trifluoro-2,4-diones 1-9 (Table 1) used as described herein were commercially available or were readily prepared by trifluoroacetylation of methyl ketones following procedures known in the art (Sloop, et al. *J. Fluorine Chem.* 2006, 127, 780; Danheiser, et al. *J. Org. Chem.* 1990, 55, 1959), such as is shown in the following example:

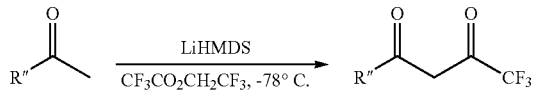

It is believed that the 1,1,1-trifluoro-2,4-diones 1-9 exist exclusively in the enol form (Sloop, et al. *J. Fluorine Chem.* 2006, 127, 780).

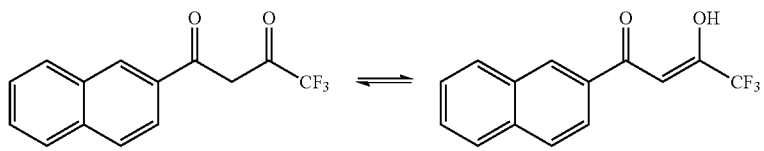 [SMILES: O=C(CC(=O)C(F)(F)F)c1ccc2ccccc2c1 ; O=C(/C=C(\O)C(F)(F)F)c1ccc2ccccc2c1]

Example 2

Synthesis of Highly α-Fluorinated Gem-Diols

The requisite substrates were prepared following standard procedures known in the art (Baumann, et al. *Tetrahedron* 2009, 65, 6611), under neutral conditions using 2.5 equivalents of Selectfluor and the 1,1,1-trifluoro-2,4-diones 1-9 shown in Table 1. This transformation was markedly efficient (81-99% yields) and devoid of intermediates from partial fluorination. It was also observed that, if one equivalent of Selectfluor is used, only starting material and products with two additional fluorines are isolated. Additionally, silica chromatography was not necessary for the purification of products 10-12, 14, and 15. The crystalline compound 14 provided further structural data following X-ray analysis and the data may support the presence of the gem-diol rather than a hydrate (FIG. 1).

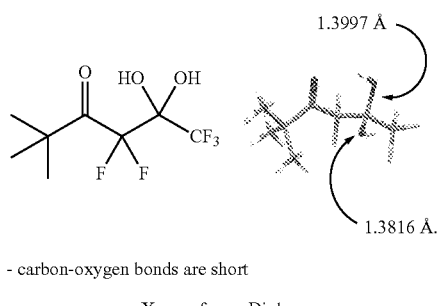

FIG. 1

Structure of gem-diol confirmed

- carbon-oxygen bonds are short

X-ray of gem-Diol.

TABLE 1

Synthesis of highly α-fluorinated gem-diols.[a]

| entry | substrate | product | yield[b] |
|---|---|---|---|
| 1 | 1 (2-naphthyl enol) | 10 | 99% |
| 2 | 2 (4-chlorophenyl enol) | 11 | 97% |
| 3 | 3 (benzodioxole enol) | 12 | 88% |
| 4 | 4 (alkenyl enol) | 13 | 99% |
| 5 | 5 (tert-butyl enol) | 14 (X-ray) | 93% |

TABLE 1-continued

Synthesis of highly α-fluorinated gem-diols.[a]

$$\underset{R''}{\overset{O}{\underset{\|}{\text{C}}}}\overset{OH}{\underset{CF_3}{\|}} \xrightarrow[CH_3CN, rt, 24 h]{\text{Selectfluor}} \underset{R''}{\overset{O}{\underset{\|}{\text{C}}}}\underset{F\ F}{\overset{HO\ OH}{\|}}\overset{}{\underset{CF_3}{\|}}$$

| entry | substrate | product | yield[b] |
|---|---|---|---|
| 6 | 6 | 15 | 91% |
| 7 | 7 | 16 | 88%[c] |
| 8 | 8 | 17 | 61%[c] |
| 9 | 9 | 18 | 82%[c] |

[a]Unless otherwise noted, reactions were performed with 2.5 equiv of Selectfluor.
[b]Isolated yield.
[c]Two-step yield from the parent methyl ketone.

Example 3

Representative Reaction Procedure for Gem-Difluorination of Various 1,3 Diketone Compounds A solution of 4,4,4-trifluoro-1-(naphthalen-2-yl)butane-1,3-dione (1) (500 mg, 1.88 mmol) in acetonitrile (12.0 ml) was treated with Selectfluor (1.66 g, 4.70 mmol). After 24 h, the reaction was diluted with EtOAc (50.0 ml) and filtered through celite. The residue was concentrated, redissolved in $CH_2Cl_2$ (20.0 ml), and washed with water (20.0 ml). The aqueous layer was extracted with $CH_2Cl_2$ (20.0 ml). Then, the organic layer was dried over $Na_2SO_4$ and concentrated under reduced pressure to give 99% yield (256.4 mg) of 2,2,4,4,4-pentafluoro-3,3-dihydroxy-1-(naphthalen-2-yl)butan-1-one (10): $^1$H NMR (500 MHz, $CDCl_3$) δ 8.70 (s, 1H), 8.02 (d, J=8.5 Hz, 1H), 7.96 (d, J=8.0 Hz, 1H), 7.87-7.84 (m, 2H), 7.67-7.64 (m, 1H), 7.58-7.55 (m, 1H), 5.27 (br s, 2H); $^{13}$C NMR (125 MHz, $CDCl_3$) δ 191.0 (t, $J_{CF}$=28.5 Hz, 1C), 136.2, 133.8 (t, $J_{CF}$=4.9 Hz, 1C), 131.8, 130.1, 129.9, 128.6, 128.3 (t, $J_{CF}$=165.0 Hz, 1C), 127.6, 127.1, 124.2, 121.8 (q, $J_{CF}$=311.9 Hz, 1C), 111.2 (t, $J_{CF}$=267.6 Hz, 1C), 92.9 (q, $J_{CF}$=26.8 Hz, 1C); $^{19}$F NMR (282 MHz, $CDCl_3$) δ −80.4 (t, J=11.3 Hz, 3F), −110.7 (q, J=11.3 Hz, 3F); IR (film) $v_{max}$ 3435, 1683, 1626, 1597, 1470 $cm^{-1}$; HRMS (ESI) m/z calcd for $C_{14}H_9F_5O_3$ (M+Na)$^+$ 343.0370, found 343.0368.

Example 4

Trifluoroacetate-Release from α-Fluorinated Gem-Diols

Trifluoroacetate-release was found to be promoted rapidly using $Et_3N$ and a salt, such as LiBr. Thus, trifluoroacetate was released from substrate 10 almost instantaneously at room temperature using LiBr and $Et_3N$ (see conditions below) to give conversion to the difluorinated compound 19 and the "self" aldol product.

Example 5

Trifluoroacetate-Release with Deuteration of Intermediate

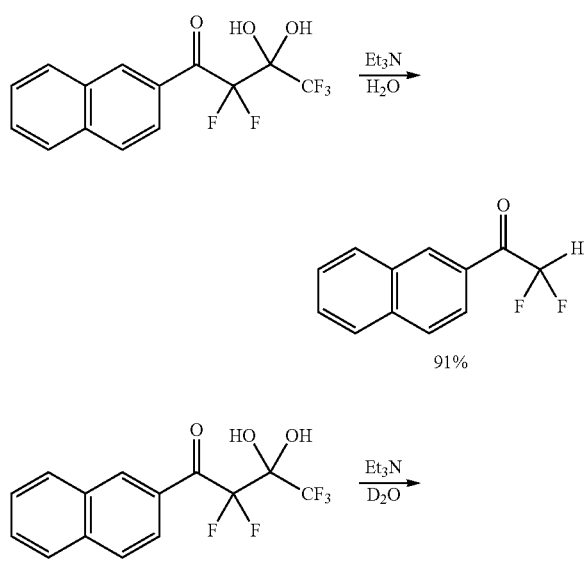

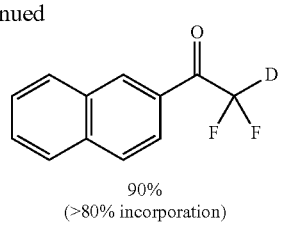

90%
(>80% incorporation)

Example 6

Aldol Reactions Between α-Fluorinated Gem-Diols Substrates and Aldehydes

Aldol reactions between α-fluorinated gem-diol substrates 10-18 and aldehydes 21-31 (Table 2) were carried out in the presence of Et₃N and LiBr in THF as solvent. Good to excellent yields (62-89%) of the aldol adduct(s) were isolated. Aryl and alkyl aldehydes seemed to be fully compatible with this process as well as α,β-unsaturated aldehyde 22 and the sensitive dienal 23. Other sensitive aldehydes also seemed to react smoothly with the α,α-difluoroenolates. It was observed that no C17 epimerization occurred for the triene 39 was isolated in 78% yield from the unsaturated starting material 13.

Example 7

Aldol Reactions with α,α-Difluoroenolates Generated from Trifluoroacetate Release

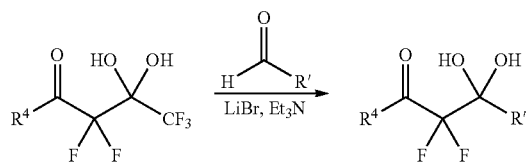

| entry | substrate | aldehyde | major product | yield[b] |
|---|---|---|---|---|
| 1 | 10 | 21 | 32 | 84% |
| 2 | 10 | 22 | 33 | 85% |
| 3 | 10 | 23 | 34 | 89% |

-continued

| entry | substrate | aldehyde | major product | yield[b] |
|---|---|---|---|---|
| 4 | 10 | cyclohexanecarboxaldehyde (24) | 35 (naphthyl ketone with CF2, OH, cyclohexyl) | 74% |
| 5 | 11 | 22 | 36 (4-chlorophenyl ketone with CF2, OH, pentenyl) | 79% |
| 6 | 12 | (S)-3-(OTIPS)butanal (25) | 37[c] (benzodioxole ketone with CF2, OH, OTIPS) | 74% (1.2:1) |
| 7 | 12 | 26 (bicyclic aldehyde) | 38 (benzodioxole ketone with CF2, OH, bicyclic) | 95% (1.2:1) |
| 8 | 13 | 23 | 39 | 78% |
| 9 | 14 | 23 | 40 (tert-butyl ketone with CF2, OH, dienyl) | 89% |
| 10 | 15 | 22 | 41 (isobutyl ketone with CF2, OH, pentenyl) | 64% |

-continued
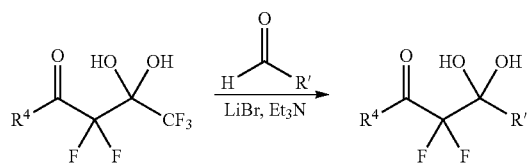
| entry | substrate | aldehyde | major product | yield[b] |
|---|---|---|---|---|
| 11 | 15 | OHC-(hexyl chain)  27 | (isobutyl ketone with CF2 and OH, hexyl chain)  42 | 72% |
| 12 | 16 | OHC-C6H4-C(O)CH3  28 | (adamantyl ketone CF2 with 4-acetylphenyl carbinol)  43 | 89% |
| 13 | 16 | OHC-CH=CH-Ph  29 | (adamantyl ketone CF2 with styryl carbinol)  44 | 84% |
| 14 | 17 | OHC-C6H4-NO2  30 | (bornyl ketone CF2 with 4-nitrophenyl carbinol)  45 | 89% (6.8:5.6: 1.1:1)[a] |
| 15 | 18 | 30 | (dimethylnorbornyl ketone CF2 with 4-nitrophenyl carbinol)  46 | 78% (1.1:1) |

-continued

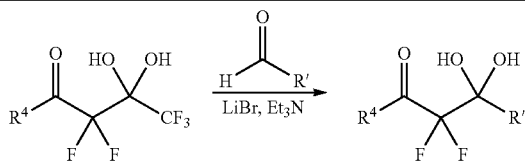

| entry | substrate | aldehyde | major product | yield[b] |
|---|---|---|---|---|
| 16 | 18 | OHC-CH(CH₃)-Ph (31) | (structure shown) | 69%[f] (9:1: 0.5)[g] 47[d] |

[a]Reactions were typically performed with 3 equiv of LiBr and 1 equiv of Et₃N.
[b]Isolated yields and diastereomeric ratio (dr) based on $^{19}$F NMR analysis of unpurified reaction products.
[c]Absolute stereochemistry determined after desilylation and cyclization.
[d]Ratio of diastereomers is 45:45:46:46.
[f]Yield determined after acid-promoted hydrolysis of hemi-acetal.
[g]Diastereomeric ratio is (R,R)-isomer/(S,R)-isomer/(S,S)-isomer.

Example 8

Representative Reaction Procedure for Aldol Type Coupling Reaction Between Various α,α,γ,γ,γ-Pentafluoro-β,β-Dihydroxy Compounds and Various Aldehydes To a solution of 2,2,4,4,4-pentafluoro-3,3-dihydroxy-1-(naphthalen-2-yl)butan-1-one (10) (30.0 mg, 0.094 mmol) and lithium bromide (24.4 mg, 0.28 mmol) in THF (600 µL), p-anisaldehyde (23.0 µL, 0.19 mmol) was added and the mixture was stirred for 30 min at room temperature under nitrogen. Et₃N (13.0 µL, 0.094 mmol) was added dropwise. After 3 min, the reaction was quenched with saturated aqueous NH₄Cl (2.0 mL) at the same temperature and the resultant mixture was extracted with EtOAc (2.0 mL×5). The organics were dried over Na₂SO₄ and concentrated under reduced pressure. SiO₂ flash chromatography (8.5:1.5-9:1 hexanes/EtOAc) afforded the desired product (32) in 84% yield (27 mg). $^1$H NMR (500 MHz, CDCl₃) δ 8.62 (s, 1H), 8.04 (d, J=8.5 Hz, 1H), 7.94 (d, J=8.0 Hz, 1H), 7.90-7.86 (m, 2H), 7.66-7.62 (m, 1H), 7.56-7.55 (m, 1H), 7.46 (d, J=8.5 Hz, 2H), 6.94-6.91 (m, 2H), 5.41-5.34 (m, 1H), 3.81 (s, 3H), 3.05 (d, J=4.5 Hz, 1H); $^{13}$C NMR (125 MHz, CDCl₃) δ 190.8 (t, J$_{CF}$=29.3 Hz, 1C), 160.1, 136.1, 133.3 (t, J$_{CF}$=5 Hz, 1C), 132.2, 130.2, 129.6, 129.5, 129.4, 128.5, 127.7, 127.0 (2), 126.7, 124.7, 116.0 (dd, T$_{CF}$=262.8, 254.5 Hz, 1C) 113.8 (2), 73.1 (dd, J$_{CF}$=28.3, 22.9 Hz, 1C), 55.3; $^{19}$F NMR (282 MHz, CDCl₃) δ −103.3 (dd, J=289.9, 5.9 Hz, 1F), −114.6 (dd, J=290.2, 18.3 Hz, 1F); IR (film) ν$_{max}$ 3468, 2934, 1690, 1626, 1612, 1465, 1177 cm$^{-1}$; HRMS (EI) m/z calcd for C₂₀H₁₆F₂O₃ (M)$^+$ 342.1068, found 342.1070.

Example 9

Aldol Reactions with Substrates 10-18 and Aldehydes 21-31 Using the Trifluoroacetate-Release Strategy Mild enolization protocols for aldol reactions have been recently reported by Coltart and co-workers (Sauer, et al. *J. Am. Chem. Soc.* 2010, 132, 13997-13999). For trifluoroacetate release, it appears that the scope may be equally impressive for the highly fluorinated substrates 10-18, because each seemed to readily participate in the process. Also, it appears that trifluoroacetate release may be quite fast, and the reactions were typically completed after 3 min at room temperature or 30 min at −78° C. Good to excellent yields (64-95%) of the aldol adduct(s) were routinely isolated. Both aryl and alkyl aldehydes, as well as the α,β-unsaturated aldehyde 22 and the sensitive dienal 23, appeared to be fully compatible with this process. Other sensitive aldehydes also appear to have smoothly reacted with the α,α-difluoroenolates; it was observed that β-elimination did not occur with 25, and little α-epimerization (i.e, 5%) was observed with 31 after $^{19}$F NMR analysis of the crude reaction mixture. Also, the reaction with 31 appeared to display a seemingly unique tendency of product 47 to form a hemi-acetal with additional aldehyde (this side-product was readily hydrolyzed with aqueous acid).

In case of the highly sensitive cis-myrtenol-derived substrate 17 (the trans-myrtenol derivative 18 is not susceptible to α-epimerization but provided adduct 46 to contrast with 45) (Peterson, et al. *J. Org. Chem.* 1991, 56, 16-20) 15% of the product mixture was the trans-isomer. Even though α-deprotonation appears to have been observed with ketone 17, the two fluorines adjacent to the ketone seem to enhance the irreversible tendency for the cis-myrtenol to convert to the trans-myrtenol. Therefore, without being bound by theory, it appears that the conditions herein were compatible with this highly sensitive substrate. This strategy appears to be quite chemoselective for aldehydes, because the keto-aldehyde 28 seems to provide only the product 43 from aldehyde addition.

Also, all of the products 32-47 have a ketone that is additionally activated by two α-fluorines, yet these aldol-adducts do not seem to out-compete the aldehydes. It is believed that further evidence of the mild reaction conditions may be available from the triene 39 that was isolated in good 78% yield from the unsaturated starting material 13. Assignment of the absolute stereochemical configuration of 47 using the traditional Mosher method (i.e., with MTPA esters) was not clear. Existing literature precedents suggest such an analysis on some fluorinated substrates may not be straightforward (Seco, et al. *Chem. Rev.* 2004, 104, 17-117; Takagi, et al. *Tetrahedron Lett.* 2000, 41, 7889-7892). However, using the recent reported comparisons of Hoye and coworkers (Hoye, et al. *Org. Lett.* 2010, 12, 1768-1771) preparation of the MPA-derivatives of to 47 allowed assignment of the absolute configuration.

Example 10

Imino-Aldol Process

Reaction conditions were similar to the above.

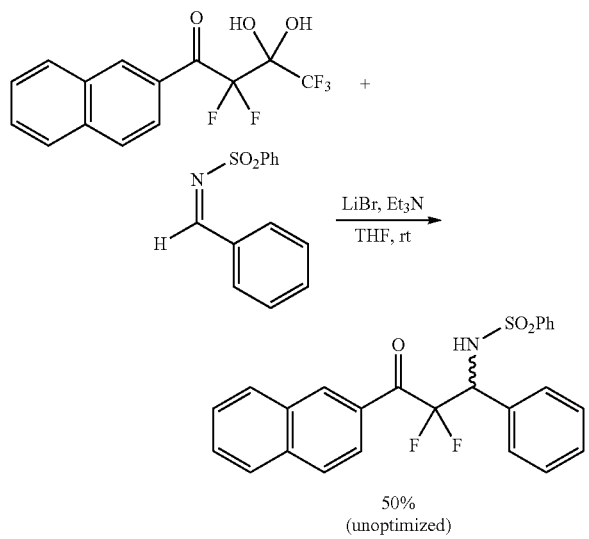

50%
(unoptimized)

Example 11

Extension of the Trifluoroacetate-Release Reaction to Other Substrates

The trifluoroacetylated ketone 1 was mono-brominated following a published procedure (Le, Q. T. H.; Umetani, S.; Suzuki, M.; Matsui, M., *J. Chem. Soc., Dalton Trans.* 1997, 643-647), stirred over water, and then the crude reaction mixture was immediately treated with LiBr and Et$_3$N in the presence of 4-nitrobenzaldehyde (see scheme below). The reaction was complete in 10 min at room temperature and the Darzens product 48 was isolated in good 65% yield (from 1) as a single diastereomer. Without being bound by theory, it is believed that high diastereoselectivity is observed during the addition of α-bromoenolates to aldehydes (Barluenga, et al. *J. Org. Chem.* 1999, 64, 5048-5052). Thus, and without being bound by theory, it is believed that the trifluoroacetate-release reaction herein is not limited to the generation of α,α-difluoroenolates and the production of α,α-difluoroketones, but presents additional synthetic opportunities with other substrates.

Example 12

To probe the mechanism of the trifluoroacetate-release strategy, a series of control reactions were performed to verify that the aldol reaction is not a stepwise process in which trifluoroacetate release occurs, followed by deprotonation of the α,α-difluoroketone, and addition to the aldehyde. Indeed, the α,α-difluoroketone 19 appeared to not react with aldehyde 21 using the trifluoroacetate-release conditions (LiBr/Et$_3$N) or other combinations of reagents (eq 2 below).

Also, it was probed whether a retro-aldol process occurs under the reaction conditions, and the aldol adduct 32 was recovered without the presence of any products from a retro-aldol reaction with benzaldehyde (eq 3 below). Without being bound by theory, these mechanistic data may be taken as further highlighting the powerful, yet mild process of trifluoroacetate release to generate reactive intermediates.

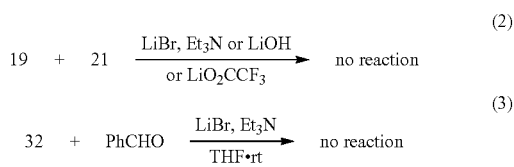

Example 13

Formation of Hexafluoroacetone Hydrate Salts

Hexafluoroacetone hydrate can exist in two states: 1) a highly reactive, corrosive, and toxic gas and 2) a stable liquid hexafluoroacetone hydrate. The solvent hexafluoroacetone hydrate may exist as a trihydrate or a heptahydrate. Stated another way, this solvent is not free of water, and thus the major hurdle of its application is to develop a moisture-free chemical. The presence of moisture will effectively prevent the subsequent use of fluoroform, because any attempts to generate the reactive trifluoromethyl anion will fail due to extremely rapid re-protonation to fluoroform.

Organic bases were tested for the formation of a salt with hexafluoroacetone hydrate.

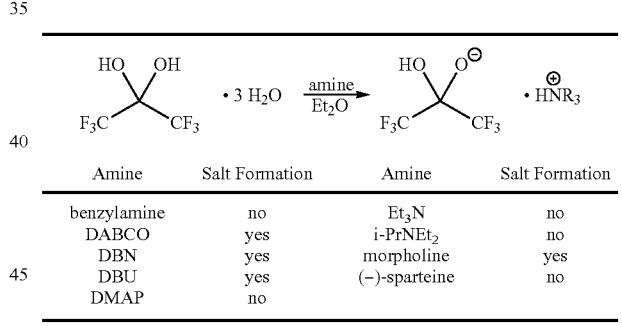

| Amine | Salt Formation | Amine | Salt Formation |
|---|---|---|---|
| benzylamine | no | Et$_3$N | no |
| DABCO | yes | i-PrNEt$_2$ | no |
| DBN | yes | morpholine | yes |
| DBU | yes | (−)-sparteine | no |
| DMAP | no | | |

The presence of water was not observed from the amine salt from DBU with hexafluoroacetone hydrate by $^1$H NMR using either CD$_3$CN or CD$_3$NO$_2$ as solvent. Indeed, this salt is stable and can be stored in a vial on the bench-top without any signs of decomposition across three months. Also, no additional water is absorbed and the salt is soluble in many common organic solvents, for example, THF, DMF, CH$_3$CN, DMSO, EtOAc, CH$_2$Cl$_2$, CHCl$_3$, and toluene.

The DBU/Hexafluoroacetone hydrate salt was prepared as follows.

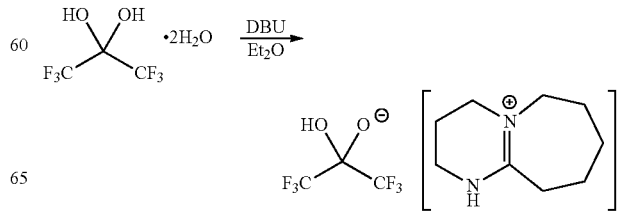

To a solution of hexafluoroacetone trihydrate (0.42 mL, 3.0 mmol) in Et₂O (3 mL) was added DBU (0.5 mL, 3.3 mmol). A white precipitate formed that was filtered, washed with Et₂O (3×2 mL), and dried to provide hexafluoroacetone hydrate salt as a white solid (892.4 mg) in 89% yield. Recrystallization from Et₂O/acetonitrile (slow evaporation) provided a crystalline solid suitable for X-ray structure analysis. $^1$H NMR (500 MHz, CD₃CN) δ 10.20 (bs, 2H), 3.44 (m, 2H), 3.39 (t, 6 Hz, 2H), 3.22 (t, 6 Hz, 2H), 2.76 (m, 2H), 1.90 (m, 2H), 1.70 (m, 2H), 1.64 (m, 4H); $^{13}$C NMR (125 MHz, CD₃CN) δ 166.6, 125.0 (q, J=294.4 Hz, 1C), 96.0 (m, 2C), 54.4, 49.1, 38.7, 32.1, 29.7, 27.4, 24.9, 20.3; $^{19}$F NMR (282 MHz, CD₃CN) δ −83.2.

Example 14

Exploration of Common Bases to Perform Trifluoromethylation Reactions

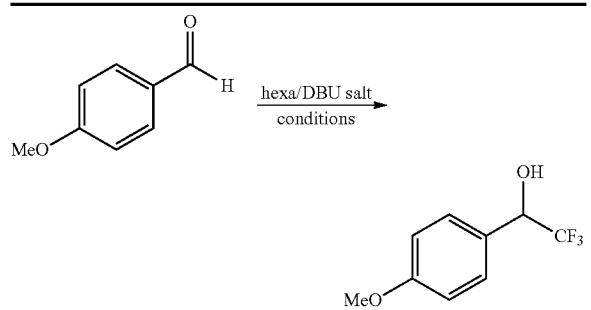

| Solvent | Base (equv) | Additive (equiv) | Temperature | % Yield$^a$ |
|---|---|---|---|---|
| DMF | KHMDS (41) | 16-crown-6 | −30 °C. | 2% |
| DMF | KH (4.4) | 18-crown-6 | −30 °C. | 17% |

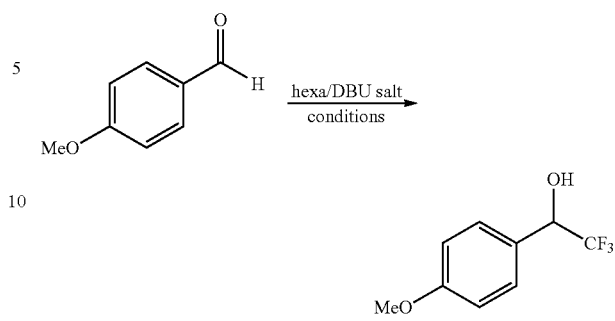

| Solvent | Base (equv) | Additive (equiv) | Temperature | % Yield$^a$ |
|---|---|---|---|---|
| DMF | dmsyl-K (2.2) | None | −20 °C. | 15% |
| DMF | t-BuOK (4.0) | 18-crown-6 (1.0) | −20 °C. | 52% |
| DMF/THF | t-BuOK (4.0) | 18-crown-6 (1.0) | −30 °C. | 31% |
| THF | t-BuOK (4.0) | 18-crown-6 (1.0) | −30 °C. | 0% |
| DMF/toluene | t-BuOK (4.0) | 18-crown-6 (1.0) | −30 °C. | 31% |
| toluene | t-BuOK (4.0) | 18-crown-6 (1.0) | −30 °C. | 44% |
| DMF | t-BuOK (4.0) | 18-crown-6 (2.0) | −20 °C. | 52% |
| DMF | t-BuOK (4.4) | Bu₄NCl (4.4) | −30 °C. | 80% |

$^a$Yields determined by $^{19}$F NMR using α,α,α-trifluorotoluene as internal standard.

Example 15

Trifluoromethylation by DBU/Hexafluoroacetone Hydrate Salt

| Entry | Substrate | Product | Yield$^a$ |
|---|---|---|---|
| 1 | 4-MeO-C₆H₄-CHO | 4-MeO-C₆H₄-CH(OH)CF₃ | 80%$^b$ |
| 2 | 2-OMe-3,4-(MeO)₂-C₆H₂-CHO | 2-OMe-3,4-(MeO)₂-C₆H₂-CH(OH)CF₃ | 95% |
| 3 | 4-Me₂N-C₆H₄-CHO | 4-Me₂N-C₆H₄-CH(OH)CF₃ | 87% |

-continued
| Entry | Substrate | Product | Yield[a] |
|---|---|---|---|
| 4 | 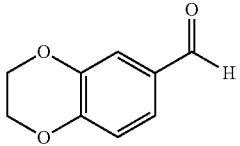 [SMILES: O=Cc1ccc2c(c1)OCCO2] | 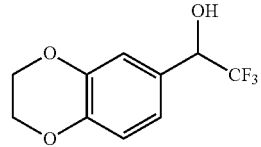 [SMILES: OC(c1ccc2c(c1)OCCO2)C(F)(F)F] | 72% |
| 5 | 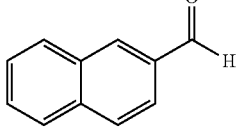 | 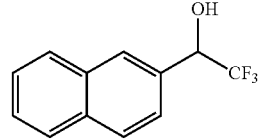 [SMILES: OC(c1ccc2ccccc2c1)C(F)(F)F] | 83%[b] |
| 6 | 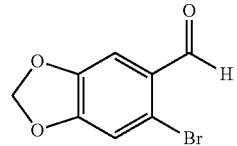 [SMILES: O=Cc1cc2c(cc1Br)OCO2] | 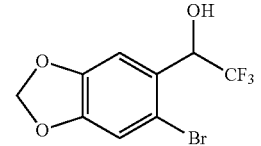 [SMILES: OC(c1cc2c(cc1Br)OCO2)C(F)(F)F] | 80% |
| 7 | 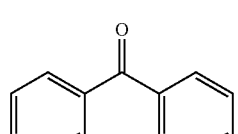 | 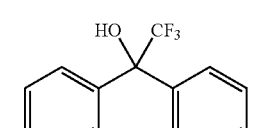 | 94% |
| 8 | 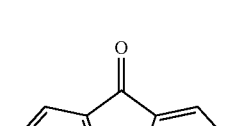 | 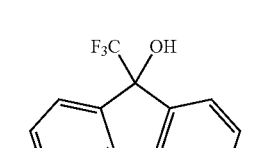 | 88% |
| 9 | 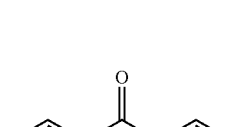 | 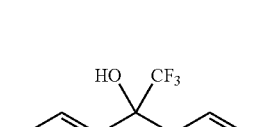 | 78% |
| 10 | 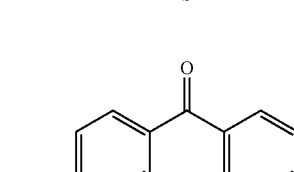 | 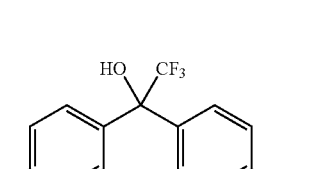 | 94% |
[a]Isolated yield;
[b]19F NMR yields (α,α,α-trifluorotoluene as internal standard).

Example 16

Olefination by Trifluoroacetate Release

| Substrate | Product | Yield |
|---|---|---|
| 1-phenyl-4,4,4-trifluoro-1,3-butanedione | phenyl vinyl ketone | 95%, |
| 1-(4-chlorophenyl)-4,4,4-trifluoro-1,3-butanedione | 1-(4-chlorophenyl) vinyl ketone | 97%, |
| 1-(naphthalen-2-yl)-4,4,4-trifluoro-1,3-butanedione | 1-(naphthalen-2-yl) vinyl ketone | 71% |
| 1-(thiophen-2-yl)-4,4,4-trifluoro-4-hydroxy-but-2-en-1-one | 1-(thiophen-2-yl) vinyl ketone | 98% |
| camphor-trifluoroacetyl derivative | camphor methylene derivative | 95%[a] |
| 1-(benzo[d][1,3]dioxol-5-yl)-4,4,4-trifluoro-1,3-butanedione | 1-(benzo[d][1,3]dioxol-5-yl) vinyl ketone | 70%[a] |

Example 17

Two-Step Detrifluoroacetylative Olefination

| entry | starting material | product | yield[a] |
|---|---|---|---|
| 1 | propiophenone | 2-methylene-1-phenylpropan-1-one | 92% |
| 2 | 1-(adamantan-1-yl)ethanone | 1-(adamantan-1-yl)prop-2-en-1-one | 88% |
| 3 | indan-1-one | 2-methyleneindan-1-one | 98% |
| 4 | carvone derivative | methylene carvone derivative | 85% |
| 5 | thujone derivative | methylene thujone derivative | 82% |
| 6 | pyrrolidinone derivative | methylene pyrrolidinone derivative | 82%[b] |

-continued

| | | | |
|---|---|---|---|
| R^m group with ketone and R^n | 1. LiMDS, CF$_3$CO$_2$CH$_2$CF$_3$  2. (CH$_2$O)$_n$ | → | R^m group with enone and R^n |

| entry | starting material | product | yield$^a$ |
|---|---|---|---|
| 7 | Boc-N 7-membered lactam | Boc-N 7-membered lactam with exo-methylene | 83% |
| 8 | bicyclic lactone | bicyclic lactone with exo-methylene | 66%$^b$ |
| 9 | γ-lactone with C$_6$H$_{13}$ | γ-methylene lactone with C$_6$H$_{13}$ | 70%$^b$ |

$^a$All yields refer to isolated, pure products.
$^b$Trifluoroacetylation was conducted at −78° C.

Example 18

Olefination of Complex Natural Products

| | | | defination yield$^a$ | |
|---|---|---|---|---|
| entry | substrate | product | via formylation | via trifluoro-acetylation$^b$ |
| 1 | labdane lactone | labdane α-methylene lactone | 28% | 65% |
| 2 | EtO$_2$C-N tropinone derivative | EtO$_2$C-N bis-methylene tropinone | 0% | 85% |
| 3 | TBSO-pregnenolone | TBSO-pregnadienone (vinyl ketone) | 36% | 64% |
| 4 | TBSO-androstenone | TBSO-androstenone with exo-methylene | trace | 59% |

| entry | substrate | product | defination yield[a] via formylation | via trifluoroacetylation[b] |
|---|---|---|---|---|
| 5 | | | 0% | 28% |

[a] All yield refer to isolated, pure products.
[b] LiHMDS, CF₃CO₂CH₂CF₃, THF, then K₂CO₃, (CH₂O)ₙ, 18-crown-6, benzene, reflux.
[c] See Murray, et al. *Synthesis* 1985, 35-38.

Example 19

General Procedure A for Detrifluoroacetylative Olefination

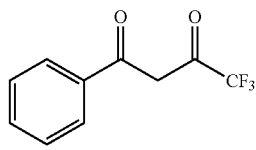 [SMILES: O=C(CC(=O)C(F)(F)F)c1ccccc1]

To a solution of 4,4,4-trifluoro-1-phenyl-1,3-butanedione (42 mg, 0.19 mmol) in benzene (10 mL) were added $K_2CO_3$ (82 mg, 0.59 mmol) and paraformaldehyde (200 mg, 6.59 mmol), and the mixture was heated to reflux (oil bath=90° C.). After 2 h the reaction mixture was allowed to cool to room temperature, saturated aqueous $NH_4Cl$ (10 mL) was added, and the resulting mixture was extracted with EtOAc (3×10 mL). The organics were dried over $Na_2SO_4$ and concentrated under reduced pressure. $SiO_2$ flash chromatography (15% EtOAc in hexanes) afforded the phenyl vinyl ketone 12 as a yellow oil (24 mg) in 93% yield.

Example 20

General Procedure B for Detrifluoroacetylative Olefination

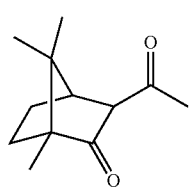

To a solution of 3-(trifluoroacetyl)camphor (45 mg, 0.19 mmol) in benzene (10 mL) were added $K_2CO_3$ (82 mg, 0.59 mmol), 18-crown-6 (13 mg, 0.05 mmol), and paraformaldehyde (200 mg, 6.59 mmol). The suspension was heated to 80° C. for 2 h and then heated to reflux (oil bath=90° C.) for 4 h. The mixture was allowed to cool to room temperature, saturated aqueous $NH_4Cl$ (10 mL) was added, and the resulting mixture was extracted with EtOAc (3×10 mL). The organics were dried over $Na_2SO_4$ and concentrated under reduced pressure. $SiO_2$ flash chromatography (5% $Et_2O$ in hexanes) afforded the α-methylene camphor as a pale yellow oil (32 mg) in 95% yield.

Example 21

General Procedure C for Trifluoroacetylation/Detrifluoroaceylative Olefination

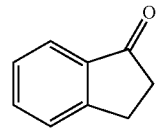

To a 0° C. solution of LiHMDS (0.65 mL, 0.6 M in THF) was added a solution of 1-indanone (26 mg, 0.19 mmol) in THF (1.0 mL). The reaction mixture was allowed to warm to room temperature over 20 min, and then $CF_3CO_2CH_2CF_3$ was added (55 µL, 0.41 mmol). After an additional 20 min at room temperature, saturated aqueous $NH_4Cl$ (5 mL) was added, and the resulting mixture was extracted with EtOAc (3×5 mL). The organics were dried over $Na_2SO_4$ and concentrated under reduced pressure. Without purification, the crude mixture was immediately subjected to general procedure B. $SiO_2$ flash chromatography (25% EtOAc in hexanes) afforded the 2-methlyene-1-indanone as a yellow oil (28 mg) in 98% yield.

Example 22

Phenyl Vinyl Ketone

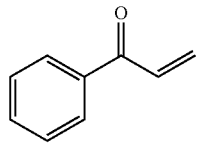

See representative reaction procedure A. $^1$H NMR, $^{13}$C NMR, and LRMS data were identical with the reported data (Guan, et al. *J. Am. Chem. Soc.* 2005, 127, 18004-18005).

Example 23 p-Chlorophenyl Vinyl Ketone

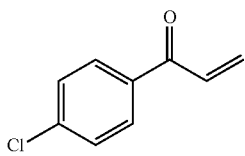

See representative reaction procedure A. SiO$_2$ flash chromatography (5% Et2O in hexanes) afforded the title compound as a clear oil (27 mg) in 83% yield. $^1$H NMR and IR data were identical with the reported data (Itoh, et al. *Bull. Chem. Soc. Jpn.* 1991, 64, 2965-2977).

Example 24

Naphthyl Vinyl Ketone

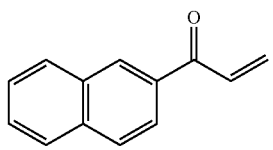

See representative reaction procedure A. SiO$_2$ flash chromatography (20% Et$_2$O in hexanes) afforded the title compound as a yellow oil (27 mg) in 76% yield. $^1$H and $^{13}$C NMR data were identical with the reported data (Matsuno, et al. *chem. Commun.* 2005, 2399-2401).

Example 25

Thienyl Vinyl Ketone

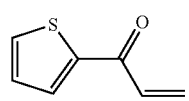

See representative reaction procedure A. SiO$_2$ flash chromatography (10% Et2O in hexanes) afforded the title compound as a colorless oil (26 mg) in 98% yield. $^1$H NMR, IR, and LRMS data were identical with the reported data (Kang, et al. *Synthesis* 1998, 823-825).

Example 26

1,3-Benzodioxoly Vinyl Ketone

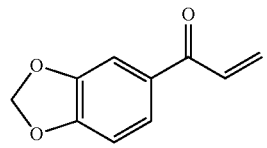

See representative reaction procedure B. SiO$_2$ flash chromatography (15% EtOAc in hexanes) afforded the title compound as a colorless oil (20.9 mg) in 61% yield: $^1$H NMR (500 MHz, CDCl$_3$) δ 7.57 (d, J=1.5 Hz, 1H), 7.46 (d, J=1.5 Hz, 1H), 7.12 (dd, J=17.0, 10.5 Hz, 1H), 6.87 (d, J=8.0 Hz, 1H), 6.42 (dd, J=17.0, 1.5 Hz, 1H), 6.06 (s, 2H), 5.87 (dd, J=10.5, 2.0 Hz, 1H); $^{13}$C NMR (125 MHz, CDCl$_3$) δ 188.8, 151.9, 148.3, 132.0 (2), 129.5, 125.1, 108.5, 107.9, 101.9; IR (film) ν$_{max}$ 2900, 1661, 1443, 1250 cm$^{-1}$; HRMS (EI) m/z calcd for C$_{10}$H$_8$O$_3$ (M)$^+$ 176.0473, found 176.0470.

Example 27

α-Methylene-camphor

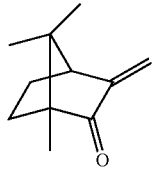

See representative reaction procedure B. $^1$H NMR and IR data were identical with the reported data (Tonari, et al. *J. Oleo Sci.* 2002, 52, 255-258).

Example 28

2-Methyl-1-phenylprop-2-ene-1-one

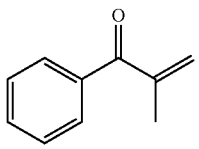

See representative reaction procedure C. SiO$_2$ flash chromatography (5% EtOAc in hexanes) afforded the title compounds as a colorless oil (26 mg) in 92% yield. $^1$H NMR, IR, and HRMS data were identical with the reported data (Rodrigues, et al. *Synth. Commun.* 2003, 33, 331-340).

Example 29

Adamantyl Vinyl Ketone

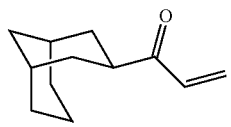

See representative reaction procedure C. SiO$_2$ flash chromatography (1% EtOAc in hexanes) afforded the title compound as a colorless oil (30 mg) in 88% yield: $^1$H NMR (300 MHz, CDCl$_3$) δ 6.83 (dd, J=17.1, 10.5 Hz, 1H), 6.32 (dd, J=17.1, 2.4 Hz, 1H), 5.63 (dd, J=10.5, 8.4 Hz, 1H), 2.06 (m, 3H), 1.81 (d, J=2.7 Hz, 6H), 1.79-1.64 (m, 6H); $^{13}$C NMR (75 MHz, CDCl$_3$) δ 204.3, 130.7, 128.6, 45.6, 38.0 (3), 36.9 (3), 28.2 (3); IR (film) $v_{max}$ 2905, 2851, 1687, 1017 cm$^{-1}$; HRMS (EI) m/z calcd for C$_{13}$H$_{18}$O (M)$^+$ 190.1358, found 190.1356.

Example 30

2-Methylene-1-indanone

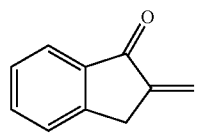

See representative reaction procedure C. $^1$H NMR, $^{13}$C NMR, IR, and HRMS data were identical with the reported data (Crich, et al. *J. Am. Chem. Soc.* 1994, 116, 8937-8951).

Example 31

α-Methylene-(R)-carvone

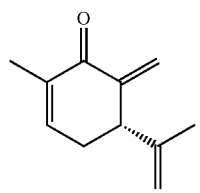

See representative reaction procedure C. SiO$_2$ flash chromatography (5% EtOAc in hexanes) afforded the title compound as a pale yellow oil (26 mg) in 85% yield: $^1$H NMR (500 MHz, CDCl$_3$) δ 6.74 (tt, J=5.0, 1.0 Hz, 1H), 6.06 (t, J=1.8 Hz, 1H), 5.19 (t, J=1.8 Hz, 1H), 4.92 (t, J=1.5 Hz, 1H), 4.77 (m, 1H), 3.39 (t, J=6.5 Hz, 1H), 2.57-2.43 (m, 2H), 1.82 (q, J=1.8 Hz, 3H), 1.71 (s, 3H); $^{13}$C NMR (125 MHz, CDCl$_3$) δ 189.0, 145.1, 144.3, 144.0, 136.0, 120.6, 113.6, 48.6, 30.0, 20.5, 16.1; IR (film) $v_{max}$ 2923, 1667, 1614, 1048 cm$^{-1}$; HRMS (EI) m/z calcd for C$_{11}$H$_{14}$O (M)+ 162.1045, found 162.1048; [α]$^{25}_D$ −31.2 (c 1.82, CH$_2$Cl$_2$).

Example 32

α-Methylene-thujone

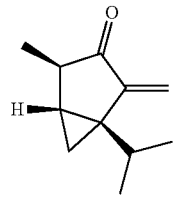

See representative reaction procedure C. SiO$_2$ flash chromatography (5% EtOAc in hexanes) afforded the title compound as a colorless oil (27 mg) in 82% yield: $^1$H NMR (500 MHz, CDCl$_3$) δ 5.60 (s, 1H), 5.31 (s, 1H), 2.35 (q, J=7.5 Hz, 1H), 1.97 (qu, J=7.0 Hz, 1H), 1.30 (dd, J=8.0, 4.5 Hz, 1H), 1.14 (d, J=7.5 Hz, 3H), 1.13 (m, 1H), 1.03 (d, J=7.0 Hz, 3H), 1.04 (d, J=7.0 Hz, 3H), 0.36 (t, J=5 Hz, 1H); $^{13}$C NMR (125 MHz, CDCl$_3$) δ 210.7, 148.5, 115.9, 45.7, 35.4, 29.7, 25.2, 20.6, 20.5, 19.1, 18.3; IR (film) $v_{max}$ 2961, 2918, 1749 cm$^{-1}$; HRMS (EI) m/z calcd for C$_{11}$H$_{16}$O (M)$^+$ 164.1201, found 164.1199; [α]$^{25}_D$ −26.1 (c 0.65, CHCl$_3$).

Example 33

N-tert-Butylcarbamate-2-methylene-ε-caprolactam

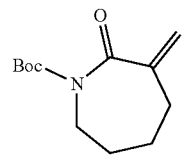 [SMILES: C=C1CCCCN(C(=O)OC(C)(C)C)C1=O]

See representative reaction procedure C. SiO$_2$ flash chromatography (50% EtOAc in hexanes) afforded the title compound as a colorless oil (36.7 mg) in 83% yield: $^1$H NMR (500 MHz, CDCl$_3$) δ 5.76 (s, 1H), 5.38 (s, 1H), 3.66 (t, J=5.0 Hz, 2H), 2.42 (t, J=5.0 Hz, 2H), 1.79-1.68 (m, 4H), 1.52 (s, 9H); $^{13}$C NMR (125 MHz, CDCl$_3$) δ 172.5, 152.7, 147.2, 123.2, 82.6, 46.0, 32.5, 29.1, 28.1 (3), 28.0; IR (film) $v_{max}$ 2934, 1761, 1707, 1180, 1141 cm$^{-1}$; HRMS (CI) m/z calcd for C$_{12}$H$_{19}$NO$_3$ (M+H—C$_4$H$_8$)$^+$ 170.0817, found 170.0814.

Example 34

(3S-cis)-(+)-Tetrahydro-3-isopropyl-7a-methyl-6-methylenepyrrolo[2,1-b]oxazol-5(6H)-one

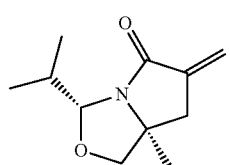

See representative reaction procedure C. The trifluoroacetylation step was conducted at −78° C. SiO$_2$ flash chromatography (15% EtOAc in hexanes) afforded the title compound as a colorless oil (31.5 mg) in 82% yield: $^1$H NMR (500 MHz, CDCl$_3$) δ 7.70 (dd, J=5.5, 3.5 Hz, 1H), 7.52 (dd, J=5.5, 3.5 Hz, 1H), 4.21 (m, 2H), 1.68 (septet, J=6.0 Hz, 1H), 1.48-1.37 (m, 2H), 1.33-1.25 (m, 4H), 0.92 (t, J=7.5 Hz, 6H); $^{13}$C NMR (125 MHz, CDCl$_3$) δ 167.7, 132.3, 130.8, 128.7, 68.0, 38.6, 30.2, 23.6, 22.9, 14.0, 10.9; IR (film) vmax 2918, 1729, 1272 cm$^{-1}$; HRMS (EI) m/z calcd for C$_{11}$H$_{17}$NO$_2$ (M)$^+$ 195.1259, found 195.1262; [α]$^{25}_D$ −0.007 (c 0.78, CHCl$_3$).

Example 35

5-Hexyl-3-methylenedihydrofuran-2(3H)-one

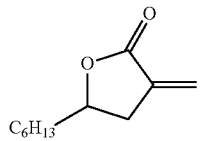

See representative reaction procedure C. The trifluoroacetylation step was conducted at −78° C. $^1$H and $^{13}$C NMR were identical with the reported data (Choudhuryi, et al. *Tetrahedron* 1999, 55, 10779-10788).

Example 36

(1S,5R)-α-Methylene-2-oxabicyclo[3.3.0]oct-6-en-3-one

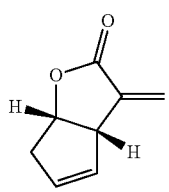

See representative reaction procedure C. The trifluoroacetylation step was conducted at −78° C. SiO$_2$ flash chromatography (25% EtOAc in hexanes) afforded the title compound as a to colorless oil (20 mg) in 66% yield: $^1$H NMR (500 MHz, CDCl$_3$) δ 6.20 (d, J=2.0 Hz, 1H), 5.76 (td, J=4.9, 2.4 Hz, 1H), 5.68 (d, J=1.7 Hz, 1H), 5.54 (dt, J=4.9, 2.1 Hz, 1H), 5.10 (t, J=6.2 Hz, 1H), 4.03 (ddt, J=5.9, 3.8, 1.9 Hz, 1H), 2.85-2.76 (m, 1H), 2.74-2.65 (m, 1H); $^{13}$C NMR (125 MHz, CDCl$_3$) δ 170.1, 136.4, 130.2, 129.6, 121.9, 80.1, 50.8, 39.4; IR (film) v$_{max}$ 2923, 1762, 1665, 1400, 1016 cm$^{-1}$; HRMS (EI) m/z calcd for C$_8$H$_8$O$_2$ (M)$^+$ 136.0524, found 136.0526; [α]$^{25}_D$=−25.3 (c 0.14, CHCl$_3$).

Example 37

11-Methylene-(+)-sclareolide

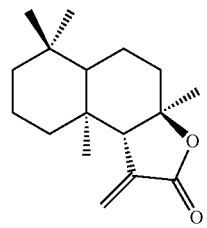

See representative reaction procedure C. SiO$_2$ flash chromatography (15% EtOAc in hexanes) afforded the title compound as a yellow oil (32 mg) in 65% yield: $^1$H NMR (500 MHz, CDCl$_3$) δ 6.13 (d, J=3.5 Hz, 1H), 5.47 (d, J=3.5 Hz, 1H), 2.51 (t, J=3.0 Hz, 1H), 2.10 (dt, J=12.0, 3.5 Hz, 1H), 1.96 (dtd, J=13.0, 3.5, 1.5 Hz, 1H), 1.89 (ddd, J=14.5, 4.0, 3.0 Hz, 1H), 1.78-1.66 (m, 2H), 1.52-1.33 (m, 3H), 1.29 (s, 3H), 1.25-1.15 (m, 2H), 1.08 (dd, J=13.0, 3.0 Hz, 1H), 1.05 (s, 3H), 0.89 (s, 3H), 0.85 (s, 3H); $^{13}$C NMR (125 MHz, CDCl$_3$) δ 171.5, 137.6, 118.4, 84.8, 64.2, 57.2, 42.3, 39.1, 38.2, 37.6, 33.7, 33.6, 23.8, 21.3, 20.7, 18.4, 15.6; IR (film) v$_{max}$ 2949, 1765, 1020, 930 cm$^{-1}$; HRMS (EI) m/z calcd for C$_{17}$H$_{26}$O$_2$ (M+H)$^+$ 263.2011, found 263.2002; [α]$^{25}_D$ +15.0 (c 1.45, CHCl$_3$).

Example 38

2,7-Dimethylene-tropinone

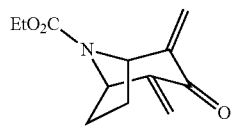 [SMILES: C=C1C(=O)C(=C)C2CCC1N2C(=O)OCC]

See representative reaction procedure C. N-ethyl carbamate tropinone was prepared to according to the literature procedure (Badio et al. *Eur. J. Pharmacol.* 1997, 321, 189-194). LiHMDS (4 equiv) and CF$_3$CO$_2$CH$_2$CF$_3$ (4 equiv) were used for trifluoroacetylation. For the olefination protocol, after heating to reflux for 4 h, the reaction mixture was cooled to 80° C., and an additional portion of paraformaldehyde (200 mg) was added. After heating at this temperature for 4 h, the reaction mixture was heated to reflux (oil bath=90° C.) for 2 h. SiO$_2$ flash chromatography (5% EtOAc in hexanes) afforded the title compound as a yellow oil (37 mg) in 85% yield: $^1$H NMR (500 MHz, CDCl$_3$) δ 6.13 (s, 2H), 5.37 (s, 2H), 4.95 (s, 2H), 4.11 (q, J=7.0 Hz, 2H), 2.32 (m, 2H), 1.76 (dd, J=8.0, 6.5 Hz, 2H), 1.21 (t, J=7.0 Hz, 3H); $^{13}$C NMR (125 MHz, CDCl$_3$) δ 187.4, 171.5, 154.3, 146.1, 146.0, 128.7, 61.8, 60.7, 59.0, 23.0, 21.4, 14.5; IR (film) v$_{max}$ 2981, 1705, 1692, 1105 cm$^{-1}$; HRMS (ESI) m/z calcd for C$_{12}$H$_{15}$O$_3$ (M+Na)$^+$ 244.0950, found 244.0948.

Example 39

α-Methylene-tert-butyl-dimethylsilyl-pregnenolone

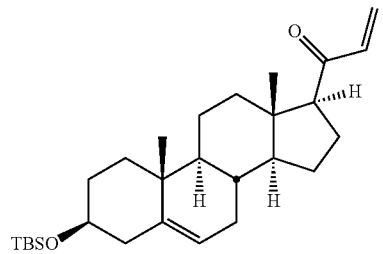

See representative reaction procedure C. The tert-butyldimethylsilyl pregnenolone was prepared according to the literature procedure (Drew, et al. *J. Org. Chem.* 1987, 52, 4047-4052). SiO$_2$ flash chromatography (4% EtOAc in hexanes) afforded the title compound as a colorless solid (55 mg) in 64% yield: mp 119-121° C.; $^1$H NMR (500 MHz, CDCl$_3$) δ 6.43 (dd, J=17.5, 10.5 Hz, 1H), 6.20 (dd, J=17.5, 1.5 Hz, 1H), 5.67 (dd, J=10.5, 1.5 Hz, 1H), 5.32 (m, 1H), 3.51-3.45 (m, 1H), 2.79 (t, J=9.0 Hz, 1H), 2.32-2.14 (m, 4H), 2.03-1.93 (m, 2H), 1.80 (dt, J=13.0, 3.5 Hz, 1H), 1.75-1.60 (m, 4H), 1.53-1.39 (m, 6H), 1.30-1.17 (m, 2H), 0.99 (s, 3H), 0.89 (s, 9H), 0.60 (s, 3H), 0.06 (s, 6H); $^{13}$C NMR (125 MHz, CDCl$_3$) δ 201.2, 141.9, 137.5, 127.4, 121.2, 72.9, 61.2, 57.6, 50.4, 45.1, 43.1, 39.4, 37.7, 37.0, 32.4, 32.3, 32.2, 26.3 (3), 25.0, 23.1, 21.4, 19.8, 18.6, 13.8, −4.2 (2); IR (film) ν$_{max}$ 2931, 1667, 1087 cm$^{-1}$; HRMS (EI) m/z calcd for C$_{28}$H$_{46}$O$_2$Si (M+H)$^+$ 443.3345, found 443.3340; [α]$^{25}_D$ +43.6 (c 0.1, CHCl$_3$).

Example 40

α-Methylene-tert-butyl-dimethylsilyl-andosterone

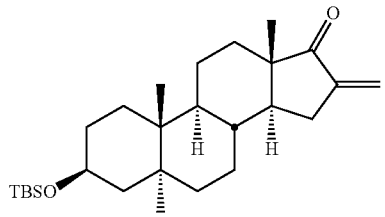

See representative reaction procedure C. The tert-butyldimethylsilyl androsterone was prepared according to the literature procedure (Izzo, et al. *Eur. J. Org. Chem.* 1999, 3505-3510). SiO$_2$ flash chromatography (2% EtOAc in hexanes) afforded the title compound as a colorless solid (47 mg) in 59% yield: mp 150-152° C.; $^1$H NMR (500 MHz, CDCl$_3$) δ 6.04 (m, 1H), 5.35 (m, 1H), 3.54 (tt, J=10.8, 5.0 Hz, 1H), 2.55 (dd, J=15.5, 6.5 Hz, 1H), 2.19-2.12 (m, 1H), 1.87-1.83 (m, 1H), 1.77-1.54 (m, 6H), 1.48-1.24 (m, 9H), 1.12-0.91 (m, 4H), 0.88 (s, 9H), 0.83 (s, 3H), 0.75-0.67 (m, 1H), 0.04 (s, 6H); $^{13}$C NMR (125 MHz, CDCl$_3$) δ 209.3, 144.9, 118.8, 72.3, 54.9, 49.0, 48.3, 45.3, 38.9, 37.4, 36.1, 34.9, 32.2, 31.9, 31.4, 29.6, 28.8, 26.3 (3), 20.8, 18.6, 14.5, 12.7, −4.2 (2); IR (film) ν$_{max}$ 2927, 2854, 1728, 1641, 1091 cm$^{-1}$; HRMS (EI) m/z calcd for C$_{26}$H$_{44}$O$_2$Si (M+H)$^+$ 417.3189, found 417.3186; [α]$^{25}_D$ +11.9 (c 2.1, CHCl$_3$).

Example 41

α-Methylene-(−)-eburnamonine

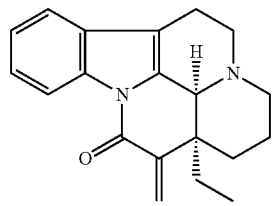

See representative reaction procedure C. SiO$_2$ PTLC (79% EtOAc; 29% hexanes; 1% Et$_3$N) afforded the title compound as a yellow oil (17 mg) in 28% yield: $^1$H NMR (500 MHz, CDCl$_3$) δ 8.45 (d, J=7.5 Hz, 1H), 7.45 (d, J=7.0 Hz, 1H), 7.36-7.28 (m, 2H), 6.66 (s, 1H), 5.73 (s, 1H), 4.14-4.12 (m, 1H), 3.36 (dd, J=14.0, 6.5 Hz, 1H), 3.28-3.22 (m, 1H), 2.98-2.91 (m, 1H), 2.64-2.60 (m, 1H), 2.57-2.47 (m, 2H), 2.36 (sextet, J=7.5 Hz, 1H), 1.93-1.83 (m, 2H), 1.45-1.40 (m, 1H), 1.38-1.25 (m, 2H), 1.01 (t, J=7.5 Hz, 3H); $^{13}$C NMR (125 MHz, CDCl$_3$) δ 162.5, 145.2, 134.8, 131.5, 130.7, 125.8, 124.7, 124.4, 118.4, 116.9, 113.1, 54.4, 51.3, 44.5, 43.2, 32.2, 24.6, 21.3, 16.9, 8.8; IR (film) ν$_{max}$ 2936, 1692, 1455, 1092 cm$^{-1}$; HRMS (EI) m/z calcd for C$_{20}$H$_{22}$N$_2$O (M)$^+$ 306.1732, found 306.1736; [[α]25$_D$ −31.4 (c 0.34, CH$_2$Cl$_2$); UV (CH$_3$CN) λ$_{max}$ (log ε) 255 (1.71), 265 (1.65) nm.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A composition comprising a base and a compound of Formula (I)

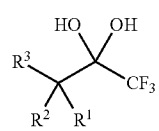

Formula (I)

wherein
R$^1$ is H, halo, or C$_{1-8}$ alkyl;
R$^2$ is H, halo, or C$_{1-8}$ alkyl; and
R$^3$ is H, halo, C$_{2-8}$ alkenyl, aryl, substituted aryl, heteroaryl, substituted heteroaryl, (CO)R$^6$, (CO)OR$^6$, (CO)SR$^6$, (CO)NR$^6$R$^7$, (SO$_2$)R$^6$, (PO)R$^6$R$^7$, or C(NR$^6$)R$^7$, wherein R$^6$ and R$^7$ are independently selected from H, C$_{1-8}$ alkyl, O—C$_{1-5}$ alkyl, C$_{3-6}$ cycloalkyl, aryl-C$_{1-5}$ alkyl, and heteroaryl-C$_{1-5}$ alkyl, aryl, substituted aryl, heteroaryl, and substituted heteoaryl
or R$^2$ and R$^3$, together with the carbon atom to which they are attached, form a 4-7 membered cycloalkyl group or cyclo(hetero)alkyl group.

2. The composition of claim 1, wherein the base is an organic base.

3. The composition of claim 1, wherein the base is an amine compound.

4. The composition of claim 1, wherein the base is DBU.

5. The composition of claim 1, wherein $R^1$ is halo and $R^2$ is halo.

6. The composition of claim 1, wherein $R^1$ is fluoro, $R^2$ is fluoro, and $R^3$ is fluoro.

7. The composition of claim 1, wherein said composition is anhydrous.

8. A hexafluoroacetone hydrate and DBU salt represented by the formula:

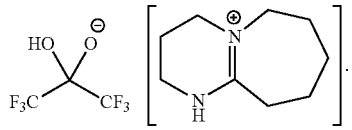

9. A process for the modification of a chemical compound via the release of trifluoroacetate, the process comprising the step of
(a) reacting the chemical compound with a composition comprising a base and a compound of Formula (I)

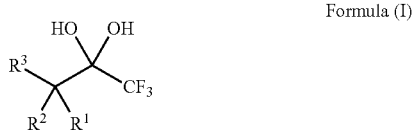

Formula (I)

wherein:
$R^1$ is H, halo, or $C_{1-8}$ alkyl;
$R^2$ is H, halo, or $C_{1-8}$ alkyl; and
$R^3$ is H, halo, $C_{2-8}$ alkenyl, aryl, substituted aryl, heteroaryl, substituted heteroaryl, $(CO)R^6$, $(CO)OR^6$, $(CO)SR^6$, $(CO)NR^6R^7$, $(SO_2)R^6$, $(PO)R^6R^7$, or $C(NR^6)R^7$, wherein $R^6$ and $R^7$ are independently selected from H, $C_{1-8}$ alkyl, O—$C_{1-5}$ alkyl, $C_{3-6}$ cycloalkyl, aryl-$C_{1-5}$ alkyl, and heteroaryl-$C_{1-5}$ alkyl, aryl, substituted aryl, heteroaryl, and substituted heteoaryl;
or $R^2$ and $R^3$, together with the carbon atom to which they are attached, form a 4-7 membered cycloalkyl group or cyclo(hetero)alkyl group.

10. A process for preparing a composition comprising a base and a compound of formula (I)

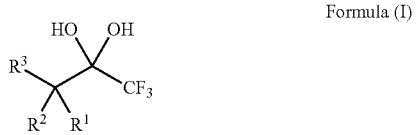

Formula (I)

wherein:
$R^1$ is H, halo, or $C_{1-8}$ alkyl;
$R^2$ is H, halo, or $C_{1-8}$ alkyl; and
$R^3$ is H, halo, $C_{2-8}$ alkenyl, aryl, substituted aryl, heteroaryl, substituted heteroaryl, $(CO)R^6$, $(CO)OR^6$, $(CO)SR^6$, $(CO)NR^6R^7$, $(SO_2)R^6$, $(PO)R^6R^7$, or $C(NR^6)R^7$, wherein $R^6$ and $R^7$ are independently selected from H, $C_{1-8}$ alkyl, O—$C_{1-5}$ alkyl, $C_{3-6}$ cycloalkyl, aryl-$C_{1-5}$ alkyl, and heteroaryl-$C_{1-5}$ alkyl, aryl, substituted aryl, heteroaryl, and substituted heteoaryl;
or $R^2$ and $R^3$, together with the carbon atom to which they are attached, form a 4-7 membered cycloalkyl group or cyclo(hetero)alkyl group,
the process comprising the step of
(a) reacting the base with the compound of Formula (I) in a solvent to form the composition.

11. The process of claim 10, wherein the base is an organic base.

12. The process of claim 10, wherein the base is DBU.

13. The process of claim 10, wherein the solvent is diethyl ether.

14. The process of claim 10, wherein the composition is the DBU/Hexafluoroacetone hydrate salt.

15. The process of claim 9, wherein the chemical compound is an aldehyde or a ketone.

16. The process of claim 9, wherein the chemical compound undergoes a trifluoromethylation reaction.

17. The process of claim 9, comprising the step of adding the base to a solution comprising the chemical compound and the compound of Formula (I).

18. The process of claim 17, wherein the chemical compound is an aldehyde.

19. The process of claim 17, wherein the base is triethylamine.

20. The process of claim 17, wherein the compound of Formula (I) is a compound of Formula (III)

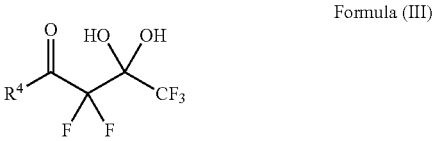

Formula (III)

wherein
$R^4$ is $R^6$, $OR^6$, $SR^6$, or $NR^6R^7$, wherein $R^6$ and $R^7$ are independently selected from H, $C_{1-8}$ alkyl, O—$C_{1-5}$ alkyl, $C_{3-6}$ cycloalkyl, aryl-$C_{1-5}$ alkyl, and heteroaryl-$C_{1-5}$ alkyl, aryl, substituted aryl, heteroaryl, and substituted heteoaryl.

* * * * *